(12) United States Patent
Hofmann et al.

(10) Patent No.: US 10,073,120 B1
(45) Date of Patent: Sep. 11, 2018

(54) INTEGRATED VACUUM-ULTRAVIOLET, MID AND NEAR-ULTRAVIOLET, VISIBLE, NEAR, MID AND FAR INFRARED AND TERAHERTZ OPTICAL HALL EFFECT (OHE) INSTRUMENT, AND METHOD OF USE

(71) Applicants: J.A. WOOLLAM CO., INC., Lincoln, NE (US); BOARD OF REGENTS OF THE UNIVERSITY OF NEBRASKA, Lincoln, NE (US)

(72) Inventors: Tino Hofmann, Harrisburg, NC (US); Mathias M. Schubert, Lincoln, NE (US); Stefan Schoeche, Lincoln, NE (US); Philipp Kuehne, Atvidaberg (SE); Craig M. Herzinger, Lincoln, NE (US); John A. Woollam, Lincoln, NE (US); Gregory K. Pribil, Lincoln, NE (US); Thomas E. Tiwald, Lincoln, NE (US); Sean R. Knight, Plattsmouth, NE (US)

(73) Assignees: BOARD OF REGENTS FOR THE UNIVERSITY OF NEBRASKA, Lincoln, NE (US), part interest; J.A. WOOLLAM CO., INC., Lincoln, NE (US), part interest ( * ) Notice: Subject to any disclaimer, the term of this patent is extended or adjusted under 35 U.S.C. 154(b) by 0 days.

(21) Appl. No.: 15/732,252

(22) Filed: Oct. 13, 2017

Related U.S. Application Data

(63) Continuation-in-part of application No. 14/545,816, filed on Jun. 24, 2015, now Pat. No. 9,851,294.

(Continued)

(51) Int. Cl.
*G01R 19/08* (2006.01)
*G06F 17/12* (2006.01)
(Continued)

(52) U.S. Cl.
CPC ............. *G01R 19/08* (2013.01); *G01N 7/00* (2013.01); *G01N 21/17* (2013.01); *G01N 21/211* (2013.01);
(Continued)

(58) Field of Classification Search
CPC .......... G01R 19/08; G01N 7/00; G01N 21/17; G01N 21/211; G06F 17/12
See application file for complete search history.

(56) References Cited

U.S. PATENT DOCUMENTS

| | | |
|---|---|---|
| 6,872,522 B1 | 3/2005 | Mecklenburg et al. |
| 7,662,560 B2 | 2/2010 | Mecklenburg et al. |
| 8,859,876 B2 | 10/2014 | Ludwig et al. |

OTHER PUBLICATIONS

Ino et al, "Terahertz time domain magneto-optical ellipsometry in reflection grometry," Oct. 28, 2003, Department of Physics, University of Joensuu, Publishes Oct. 6, 2004, Physical Review B 70, 155101 (2004), pp. 155101-1-155101-9.*

(Continued)

*Primary Examiner* — David Porta
*Assistant Examiner* — Faye Boosalis
(74) *Attorney, Agent, or Firm* — James D. Welch

(57) ABSTRACT

Optical Hall Effect (OHE) method for evaluating such as free charge carrier effective mass, concentration, mobility and free charge carrier type in a sample utilizing a permanent magnet at room temperature.

26 Claims, 14 Drawing Sheets

Related U.S. Application Data

(60) Provisional application No. 62/070,239, filed on Aug. 18, 2014.

(51) Int. Cl.
*G01N 7/00* (2006.01)
*G01N 21/17* (2006.01)
*G01N 21/21* (2006.01)

(52) U.S. Cl.
CPC ....... *G06F 17/12* (2013.01); *G01N 2021/212* (2013.01)

(56) References Cited

OTHER PUBLICATIONS

Kuhne et al, "An integrated mid-infrared, far-infrared and terahertz optical Hall effect instrument", Department of Electrical Engineering and Center for Nanohybrid Functional Materials, University of Nebraska-Lincoln, Lincoln Nebraska 68588, Jan. 15, 2017, pp. 1-20.*

Neshat et al, "Terahertz time-domain spectroscopic ellipsometry: instrumentation and calibration", Department of Physics and Astronomy, Johns Hopklins University, Dec. 14, 2012, vol. 20, No. 27 Optics Express pp. 29063-29072.*

Nagashima et al, "Measurement of Complex Optical Constants of a High Dopant Si Wafer using Terahertz Ellipsometry", Applied Physics Letters 79, No. 24, Dec. 10, 2001, pp. 3917-3919.*

Matsumoto et al, "Measurement of the dielectric constant of thin films by teraherts time-domain spectroscopic ellipsometry", Jan. 15, 2011, vol. 36, No. 2 Optics Letters, pp. 265, 1-5.*

* cited by examiner

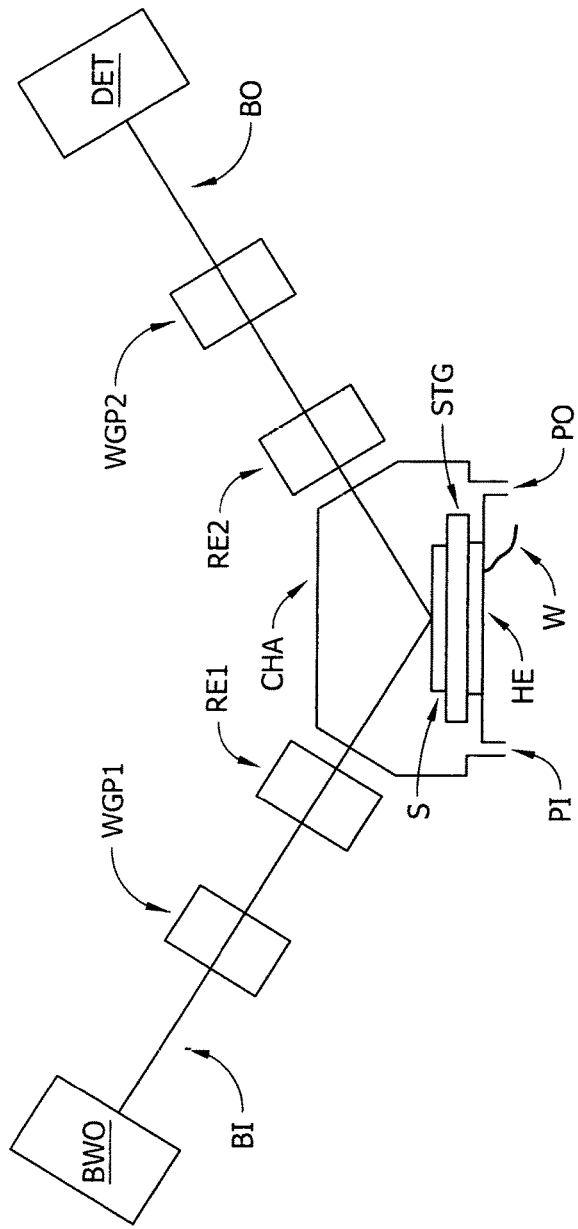
FIG. 1D
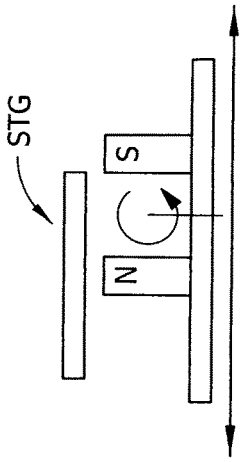
FIG. 1D'''
FIG. 1D''
FIG. 1D'

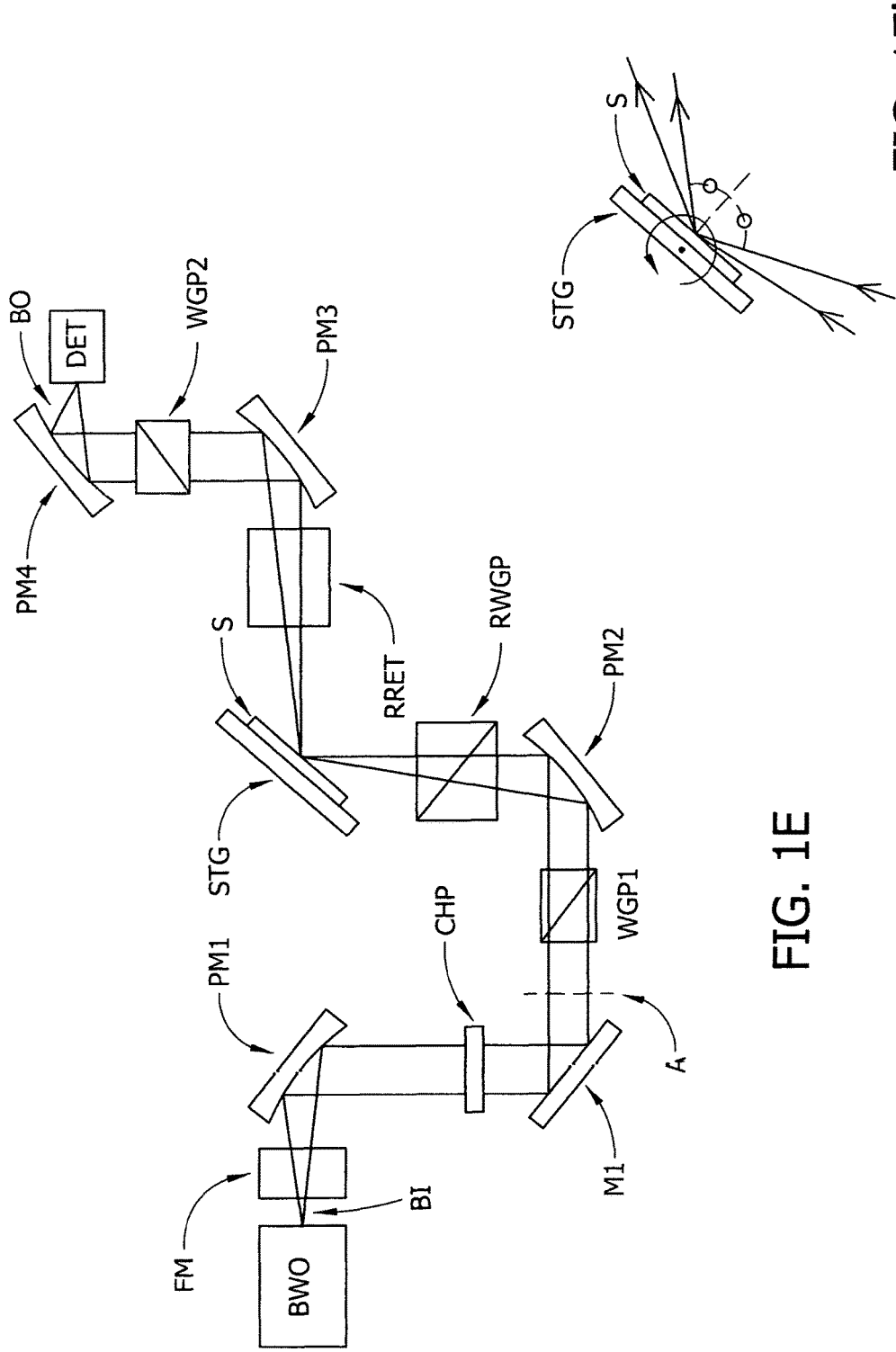

- One magnet:
  - Any AOI
  - Max surface field of magnet without iron cone: 0.52T

- Two magnets:
  - Works with AOI of ~ 70° or greater (to avoid clipping beam)
  - Max field in center of gap: ~1.15T

| $M_{11}$ | $M_{12}$ | $M_{13}$ | $M_{14}$ |
|---|---|---|---|
| $M_{21}$ | $M_{22}$ | $M_{23}$ | $M_{24}$ |
| $M_{31}$ | $M_{32}$ | $M_{33}$ | $M_{34}$ |
| $M_{41}$ | $M_{42}$ | $M_{43}$ | $M_{44}$ |

FIG. 4C

INTEGRATED VACUUM-ULTRAVIOLET, MID AND NEAR-ULTRAVIOLET, VISIBLE, NEAR, MID AND FAR INFRARED AND TERAHERTZ OPTICAL HALL EFFECT (OHE) INSTRUMENT, AND METHOD OF USE

This Application is a CIP of Allowed application Ser. No. 14/545,816 Filed Jun. 24, 2015 and Claims benefit of Provisional Application No. 62/070,239 filed Aug. 18, 2014 therevia.

SUPPORT

This invention was made with government support under W911NF-09-C-0097 awarded by the Army Research Office and under DMR0907475, EPS1004094, and DMR0922937 awarded by the National Science Foundation. The United States Government has certain rights in the invention. Additional support was provided by the University of Nebraska, the J.A. Woollam Co. and the J.A. Woollam Foundation.

TECHNICAL AREA

The present invention relates to Hall Effect measurement systems, and more particularly to an integrated Vacuum-Ultraviolet (VUV), Near (NUV) and Mid-Ultraviolet (MUV), visible (VIS), near infrared (NIR) mid-infrared (MIR), far-infrared (FIR) and terahertz (TZ) Optical Hall Effect (OHR) instrument, covering an ultra-wide spectral range from 10 nanometers to 2 millimeters, and methodology of its use in determining such as free charge carrier longitudinal and transverse effective masses, concentration, mobility and charge carrier type. Various embodiments comprise sub-systems, such as a magneto-cryostat-transfer sub-system that enables the usage of a magneto-cryostat sub-system with a (VUV), (NUV), (MUV), (VIS), (NIR), (MIR) or (THZ) ellipsometer sub-system, and a (FIR)/(THZ) ellipsometer sub-system. An electromagnetic beam (EM) providing Source sub-system can be applied to provide a variable angle-of-incidence, to a sample, in spectroscopic ellipsometers in reflection or transmission mode, and comprises, in a desired wavelength range, at least one light source and detector. The ellipsometer sub-systems can be operated in rotatable polarizer-sample-rotating-analyzer configuration granting access to the upper left 3×3 block of the normalized 4×4 Mueller matrix. The closed cycle magneto-cryostat sub-system provides sample temperatures between room temperature and 1.4 degrees K, and magnetic fields up to 8 T, enabling the detection of transverse and longitudinal magnetic field-induced birefringence, which can be enhanced by a resonance cavity effect. A preferred embodiment, which is focal in the present invention, replaces the magneto cryostat with a smaller (0.8-1.6 T) permanent magnet, and results produced therewith are easier to obtain and apply, especially in less substantial lab settings.

BACKGROUND

The Optical Hall Effect (OHE) is a physical phenomenon which describes the occurrence of transverse and longitudinal magnetic field-induced birefringence, caused by the nonreciprocal magneto-optic response of electric charge carriers. The term (OHE) is used since the classic electrical Hall Effect (HE), and the (OHE) effect both find explanation within the Drude model. The term Optical Hall Effect (OHE) is used in analogy to the classic electrical Hall Effect as the electrical Hall effect and certain cases of (OHE) observation can be explained by extensions of the classic Drude model for the transport of electrons in matter, (eg. Metals). For the (OHE), Drude's classic model is extended by a magnetic field and frequency dependency, describing the electron's momentum under the influence of the Lorentz force. As a result an anti-symmetric contribution is added to the dielectric tensor, the sign of which depends on the type of the free charge carrier (electron or hole). The non-vanishing off-diagonal elements of the dielectric tensor reflect the magneto-optic birefringence, which lead to conversion of [p]-polarized into [s]-polarized electromagnetic waves, and vice versa. The (OHE) allows determination of concentration, mobility, and effective mass of the free electrons as the (OHE) can be quantified in terms of the Mueller matrix, which characterizes the transformation of an electromagnetic wave's polarization state. Experimentally the Mueller matrix is measured by Generalized Ellipsometry (GE), which allows for adjustment of the Angle and the Plane of Incidence a beam of electromagnetic radiation makes with respect to a sample surface, as well as rotation of a sample about a perpendicular to said sample surface. Further, during a (GE) measurement different polarization states of the incident light are prepared and their change upon reflection from or transmission through a sample is determined.

Optical Hall Effect (OHE) instruments conduct GE measurements on samples in high quasi-static magnetic fields, and detect the magnetic field induced changes of the Mueller matrix. Though several instruments with partial (OHE) capability are described in the literature, most thereof do not fulfill all desirable criteria for a true (OHE) instrument. For instance, in 1985 Nederpel and Martens, published an article, (see Review of Scientific Instruments, 56,687 (1985)), reported development of a single wavelength (444 nm) magneto-optical ellipsometer for use in the visible spectral range, but the instrument provided only low magnetic fields, (ie. B less than 50 mT). An instrument providing higher magnetic fields with spectroscopic generalized ellipsometry capabilities in the visible spectral range and a vector magnet, (ie. B in the range of 0.4 T) was presented in 2003 by Cerne et al., (see Review of Scientific Instruments, 74, 4755 (2003)). This article presented a magneto-polarimetry instrument which provided a higher magnetic field strength, (ie. B up to 8 T), for use in the mid-infrared spectral range, (ie. spectral lines of a $CO_2$ laser), and in 2004 Padilla et al. developed a terahertz-visible, (ie. 6 to 20000 $cm^{-1}$ wavelength), magneto-reflectance and transmittance instrument, (ie. a B less than or equal to 9 T), (see Review of Scientific Instruments, 74, 4710, (2004)). While both instruments provide high magnetic fields, and contain polarizers and photo-elastic-modulators, these instruments were not designed to record Mueller matrix data (GE).

A THz time-domain spectroscopy based instrument capable of recording the complex reflection coefficients at magnetic B fields of about 0.5 T was described in 2004 by Ino et al., (see Phys. Rev. B 70, 155101, (2004)). A full 4×4 Mueller matrix in the terahertz-mid-infrared spectral range (20 to 4000 $cm^{-1}$) can be measured by an instrument described in 2013 by Stanislavchuk et al., (see Review of Scientific Instruments, 84, 023901, (2013)), but there the instrument was not designed for experiments with the sample exposed to external magnetic fields.

The first full (OHE) instrument was developed and demonstrated in 2006 by Inventor herein, Hofmann, (see Review of Scientific Instruments, 77, 63902, (2006)) for the far-infrared (FIR) spectral range (30 to 650 $cm^{-1}$), which provided magnetic fields up to 6 T and allowed sample temperatures between 4.2 K and room temperature. This first full capability (OHE) instrument has since been successfully used to determine free charge carrier properties including effective mass parameters for a variety of material systems. Later, (OHE) experiments were conducted in the terahertz (THz) spectral range, but were limited to room temperature and low magnetic fields (ie. B fields less than or equal to 1.8 T), and are subject of the invention disclosed herein.

Since the magnitude of the (OHE) depends on the magnetic field strength, higher magnetic fields facilitate the detection of the OHE. Furthermore, the sensitivity to the (OHE) is greatly enhanced by phonon mode coupling, surface guided waves and Fabry-Perot interferences. Since these effects appear from the THz to the mid-infrared (MIR) spectral range, depending on the structure and material of the sample, it can become necessary to extend the spectral range covered by (OHE) instrumentation. An (OHE) instrument for the MIR, for example, can detect the magneto-optic response of free charge carriers enhanced by phonon modes present in the spectral range above 600 cm$^{-1}$, which applies to many substrate materials, SiC, Al$_2$O$_3$ or GaN, as well as to many materials used for thin films, III-V nitride semiconductors Al$_{1-x}$Ga$_x$N In$_{1-x}$N Al$_{1-x}$In$_x$N or In$_{1-x}$Ga$_x$N. In addition, inter-Landau-level transitions can be studied in the MIR spectral range with a MIR (OHE) instrument. The extension to the THz spectral range enables the detection of the (OHE) in samples with low carrier concentrations. Furthermore, the strongest magneto-optic response can be observed at the cyclotron resonance frequency, which typically lies in the microwave/THz spectral range for moderate magnetic fields, (eg. a few Tesla), and effective mass values comparable to the free electron mass.

With the foregoing insight it is noted that the present invention presents an (OHE) instrument that covers an ultra-wide spectral range from 3/cm to 7000/cm, (ie. 0.1-210 THz or 0.4-870 meV), which combines MIR, FIR and THz magneto-optic generalized ellipsometry in a single instrument. This integrated MIR, FIR and THz (OHE) instrument can incorporate a commercially available, closed cycle refrigerated, superconducting 8 Tesla magneto-cryostat sub-system, with four optical ports, providing sample temperatures between T=1.4 K and room temperature. However, the preferred embodiment applies at least one permanent magnet with strength in the range of 0.6 to 1.8 T. The ellipsometer sub-systems used to actually achieve results reported herein, were built in-house and operate in the rotating-analyzer configuration, (a non-limiting election), and are capable of determining the normalized upper 3×3 block of the sample Mueller matrix. Said (OHE) provides insight into free charge carrier properties such as effective mass (m), mobility (u), and carrier concentration (N) of complex and even layered samples. It is noted that the optical Hall Effect (OHE) reveals fundamental symmetry properties of the magneto-optic dielectric tensor.

For insight it is noted that operation of the integrated MIR, FIR and THz (OHE) instrument described was demonstrated by three sample systems. Combined experimental data from the MIR, FIR and THz spectral range of a single epitaxial graphene sample, grown on a 6H-SiC substrate by thermal decomposition were achieved. The MIR (OHE) data of the same epitaxial graphene sample was investigated to demonstrate the operation of the MIR ellipsometer sub-system of the integrated MIR, FIR and THz (OHE) instrument, over the full available magnetic field range of the instrument. The magneto-optic response of free charge carriers and quantum mechanical inter-Landau-level transitions were observed, and their polarization selection rules obtained therefrom noted. A Te-doped, n-type GaAs substrate served as a model system for the FIR spectral range of the FIR/THz ellipsometer sub-system. The (OHE) signal originating from valence band electrons in a bulk material were noted, and the concentration, mobility, and effective mass parameters of the valence band electrons determined. Finally, (OHE) data from an AlGaN/GaN high electron mobility transistor structure (HEMT) from the THz spectral range of the FIR/THz ellipsometer sub-system were achieved and analyzed. The data was recorded at different temperature between T=1.5 K and room temperature, representing the full sample temperature range of the instrument. The results achieved at room temperature were especially important as regards the present invention.

In this Background Section, in what directly follows, dielectric and magneto-optic dielectric tensors are described, a brief theoretical overview on Mueller matrices and GE data-acquisition is given, and general GE data analysis procedures are introduced. In the Detailed Description and Drawing Sections of this Application a description of a relevant, but not-necessarily limiting experimental setup is described, along with data acquisition and data analysis procedures for (OHE) data, and examples of experimental results demonstrating the operation of the integrated MIR, FIR and THz (OHE) instrument are presented and discussed.

Continuing, the evaluation of physically relevant parameters from the (OHE) requires the experimental observation and quantification of the OHE, and a physical model to analyze (OHE) data. Experimentally, the (OHE) is quantified in terms of the Mueller matrix $M_{OHE}$ by employing Generalized Ellipsometry (GE). The physical model which is used to analyze the observed transverse and longitudinal magneto-optic birefringence of the (OHE) is based on the magneto-optic dielectric tensor $\epsilon_{oeh}(B)$, which is a function of the slowly varying external magnetic field B. If, among other parameters, the magneto-optic dielectric tensor of a sample is known, experimental Mueller matrices $M_{OHE}$ can be modeled from $\epsilon_{oeh}(B)$ using the relationship:

$$M_{OHE}(\epsilon_{oeh}(B))$$

Although this equation is in general not invertible analytically, it can be used to determine the magneto-optic dielectric tensor from experimental Mueller matrix data through non-linear model mathematical regression analysis. Dielectric tensors, Mueller matrix calculus, generalized ellipsometry including data acquisition, as well as data analysis are further addressed in this section.

Magneto-Optical Dielectric Tensors

The optical response of a sample is here described by the dielectric tensor $\epsilon$. If the dielectric tensor of the sample without a magnetic field is given by $\epsilon_{B=0}$ and the change of the dielectric tensor induced by a magnetic field B is given by $\epsilon_B$, the dielectric tensor describing the (OHE), can be expressed as:

$$\epsilon_{(OHE)} = \epsilon_{B=0} + \epsilon_B.$$

The magneto-optic permittivity of a material within a given sample described by $\epsilon_B$ may originate from the response of bound and unbound charge carriers subjected to the magnetic field and the action of the Lorentz force. The magneto-optic response of a sample subjected to the integrated MIR, FIR and THZz (OHE) instrument, and which is addressed herein is represented by a generally anisotropic and nonreciprocal tensor. Thus, the corresponding magneto-optic contributions $X_+$ and $X_-$ to the permittivity tensor $X = \epsilon - I$, (where I is the 3×3 identity matrix), originate from the interaction of right- and left-handed circularly polarized light with the sample, respectively. Without loss of generality, if the magnetic field B is pointing in vector direction indicated by $P=\varepsilon_0\chi E$, it can be described by arranging the electric fields in their circularly polarized eigensystem $E_e= (E_x+iE_y, E_x-iE_y, E_z)=(E+,E_-,E_z)$ by $P_e=\varepsilon_0\chi_e E_e=\varepsilon_0(\chi_+E_+, (\chi_-E_-,0)$, where $i=\text{sqrt}\{-1\}$ is the imaginary unit. Transforming $P_e$ back into the laboratory system the change of the dielectric tensor induced by the magnetic field takes the form:

$$\varepsilon_n = \frac{1}{2}\begin{pmatrix} (x++x-) & i(x+-x-) & 0 \\ -i(x++x-) & x++x- & 0 \\ 0 & 0 & 0 \end{pmatrix} \quad (3)$$

Note, under field inversion B is reversed into $-B$, the polarizabilities for left- and right-handed circularly polarized light interchange. $\varepsilon_B$ is only diagonal if $X_+=X_-$, and otherwise non-diagonal with anti-symmetric off diagonal elements.

Classic Dielectric Tensors (Lorentz-Drude Model)

Charges carriers, subject to a slowly varying magnetic field obey the classical Newtonian equation of motion (Lorentz-Drude model):

$$m\ddot{x}+m\gamma\dot{x}+m\omega_0^2 x=qE+q(\dot{x}\times B) \quad (4)$$

where m, q, $\mu=qm^{-1}\tau^{-1}$, x and $\omega$ represent the effective mass tensor, the electric charge, the mobility tensor, the spatial where m, q, $\mu=qm^{-1}\tau^{-1}$, x and $\omega$ represent the effective mass tensor, the electric charge, the mobility tensor, the spatial coordinate of the charge carrier and the Eigen-frequency of the un-damped system without external excitation and magnetic field, respectively. For a time harmonic electromagnetic plane wave with an electric field $E\rightarrow E\exp(-i\omega t)$ with angular frequency $\omega$, the time derivative of the spatial displacement of the charge carrier is $\dot{x}=v\exp(i\omega t)$, where v is the velocity of the charge carrier. With $j=nqv$ Eq. 4 reads:

$$E = 1\bigg/ nq\bigg[lm/q\omega\bigg(\omega\binom{2}{0}l - \omega^2 l - i\omega\gamma\bigg)j + (B\times j)\bigg]. \quad (5)$$

where n is the charge carrier density. With the Levi-Cevita-Symbol $\varepsilon(ijk)$, (note, in the following equation the Einstein notation is used, and the covariance tensor and contravariance is ignored since all coordinate systems are Cartesian, and the summation is only executed over pairs of lower indices), the conductivity tensor $0^-$, the dielectric constant $\varepsilon_0$, and using $E=0^{-1}_j$ and the dielectric tensor for charge carriers subject to the external magnetic field B can be expressed as:

$$\varepsilon_{\iota\kappa} = nq^2/\varepsilon n\bigg[mi\kappa\bigg(w\binom{2}{0}\bigg) - w^2 - i\omega\gamma i\kappa\bigg) - i\omega\varepsilon ijkqBj\bigg]^{-1}. \quad (6)$$

Polar Lattice Vibrations, (Lorentz Oscillator)

For isotropic effective mass tensors the cyclotron frequency can be defined, and for the mass of the vibrating atoms of polar lattice vibrations, the cyclotron frequency is several orders of magnitude smaller than for effective electron masses, and can be neglected for the magnetic fields and spectral ranges discussed in this Specification. Therefore, the dielectric tensor of polar lattice vibrations $\varepsilon^L$ can be approximated using Eq. 6 with B=0. When assuming isotropic effective mass and mobility tensors, the result is a simple harmonic oscillator function with Lorentzian-type broadening. For materials with orthorhombic symmetry and multiple optical excitable lattice vibrations, the dielectric tensor can be diagonalized to:

$$\varepsilon^L = \begin{pmatrix} \left(\varepsilon\frac{L}{X}\right) & 0 & 0 \\ 0 & \varepsilon\frac{L}{Z} & 0 \\ 0 & 0 & \varepsilon\frac{L}{Z} \end{pmatrix} \quad (7)$$

Where

Where $\varepsilon\left(\dfrac{L}{K}\right)$ for $(k-(x_1y_1z_1))$ for $(k-(x_1y_1z_1))$ is given by:

$$\varepsilon L/K = \varepsilon\infty, k\pi\binom{l}{j=1}^j = 1\omega 2 + i\omega\gamma L0, \quad (8)$$

$$kj-\omega 2L0, kj/\omega 2 + i\omega\gamma T0, kj-\omega 2T0, kj$$

Where $\omega_{LO,j,k}$, $\gamma_{LO,j,k}$, $\omega_{TO,j,k}$ and $\gamma_{TO,j,k}$ denote the k(x,y,z) component of the frequency and the broadening values of the $j^{th}$ longitudinal optical (LO) and transverse optical (TO) phonon modes, respectively, while the index j runs over 1 modes. Further details can be found in Hofmann et al., Applied Physical Letters 88, 042105 (2006); Barker, Phys. Rev., 136, A1290 (1964); Berryman et al. Phys. Rev. 174, 791, (1968); Gervais et al., J. Phys. C 7, 2374, (1974); Hofmann et al., Phys. Rev. B, 66, 19504 1 (2002) 1 and a discussion of the requirements to broadening parameters, such as Im $$\left(\varepsilon\frac{L}{K}\right)$$

greater than or equal to 0.0 are found in Kasic et al., Phys. Rev. B 61,7365, (2000).

Free Charges Carriers (Extended Drude Model)

For free charge carriers no restoring force is present and the Eigen-frequency of the system is $\omega_0=0$. For isotropic effective mass and conductivity tensors, and magnetic fields aligned along the z-axis Eq. 6 can be written in the form for B=0.

$$\omega\binom{2}{p}\bigg/\omega(\omega = i\gamma)l = \varepsilon^D l; \quad (9)$$

where $\omega_P$ is the plasma frequency, and $\varepsilon^D$ is permittivity function of the isotropic Drude dielectric function. The magneto-optic contribution to the dielectric tensor $\varepsilon^D$ for isotropic effective masses and conductivities can be expressed, using Eq. 3, through polarizability functions for right- and left-handed circularly polarized light:

$$x\pm = -(\epsilon D)/(1\pm(\omega+j\gamma/\omega c)), \quad (10)$$

where $\omega_c = q B/m$ is the isotropic cyclotron frequency.

Non-Classic Dielectric Tensors (Inter-Landau-Level Transitions)

The permittivity tensor describing the contribution of a series of inter-Landau-level transitions to the dielectric tensor can be approximated by a sum of Lorentz oscillators. The quantities in Eq. (3) are then expressed by:

$$x\pm = e^{\pm i\phi}\left(\left(\sum_k\right)\right)(A_K)/(\omega^2 - \omega^{(2/0 \cdot K)} - i\gamma K\omega), \quad (11)$$

where $A_K$, $\omega_0$, an $_K$ are amplitude, transition energy, and broadening parameter of the $K^{th}$ inter Landau-level transition, respectively, which in general depend on the magnetic field. The phase factor was introduced here to describe transition, respectively, which in general depend on the magnetic field. The phase factor was introduced here to describe the experimentally observed line shapes of all Mueller matrix elements.

For inter-Landau-level transitions in graphite or bi-layer graphene we find $\varphi = \pi/4$, and for inter-Landau-level transitions in single layer graphene $\varphi = 0$.

Note that for $\varphi = 0$, the polarizabilities for left and right handed circularly polarized light are equal, $(\chi_+ = \chi_-)$, and $$\varepsilon\frac{LL}{B}$$

is diagonal.

Mueller Matrix Calculus, GE and Data Acquisition

Generalized ellipsometry (GE) extends standard, isotropic ellipsometry (SE) to arbitrary anisotropic and depolarizing samples by including rotation about a perpendicular to a sample surface, and can reveal the complex 3×3 dielectric tensor of the material investigated. This section describes the Jones vector/Mueller matrix formalism used in GE, aspects of Mueller matrix and (OHE) data, and the acquisition of Mueller matrix data.

Stokes Vector/Mueller Matrix Calculus

The real-valued Stokes vector S has four components, carries the dimensions of intensity, and can quantify any polarization state of plane electromagnetic waves. If expressed in terms of the p- and s-coordinate system Stokes vector S has four components, carries the units of intensity, and can quantify any polarization state of plane electromagnetic waves. $I_{-45}$ and $S4=I_{o+}-I_{o-}$, with $I_p$, $I_s$, $I_{45}$ $I_{-45}$, $I_{o+}$ and $I_{o-}$ being intensities for the p-. s- +45°, -45°, right and left handed circularly polarized light components, respectively. (See R. M. Azzam and N. M. Bashara, "Ellipsometry and Polarized Light", North-Holland Publ. Co., Amsterdam, (1984)).

The real-valued 4×4 Mueller matrix M describes the change of electromagnetic plane wave properties (intensity, polarization state), expressed by a Stokes vector S, upon change of the coordinate system or the interaction with a sample, optical element, or any other matter:

$$s_i^{(out)} = \Sigma_{i=1}^3 M_{ij} S_i^{(in)}, (=1 \ldots 4), \quad (12)$$

Where $S^{(out)}$ and $S^{(in)}$ denote the Stokes vectors of the electromagnetic plane wave before and after the change of the coordinate system, or an interaction with a sample, respectively. Note that all Mueller matrix elements of the GE data discussed in this paper, are normalized by the element $M_{11}$, therefore $M_{ij}$ is less than or equal to and $M_{11}=1$.

Mueller Matrix and (OHE) Data

The Mueller matrix can be decomposed in 4 sub-matrices, where the matrix elements of the two off-diagonal-blocks:

$$\begin{bmatrix} M13 & M14 \\ M23 & M24 \end{bmatrix} = \begin{bmatrix} M21 & M14 \\ M41 & M42 \end{bmatrix}$$

only deviate from zero if p- to s- polarization mode conversion appears, while the matrix elements in the two on-diagonal-blocks:

$$\begin{bmatrix} M13 & M14 \\ M23 & M24 \end{bmatrix} = \begin{bmatrix} M21 & M14 \\ M41 & M42 \end{bmatrix}$$

mainly contain information about p- to s- polarization mode conversion, while the matrix elements in the two on-diagonal-blocks mainly contain information about p- s- polarization mode conserving processes. It is to be appreciated that p- to p- polarization mode conversion is defined as the transfer of energy from the p- polarized channel of an electromagnetic plane wave to the s- polarized channel, or vice versa. Polarization mode conversion can appear when the p- s- coordinate system is different for $S^{in}$ and $S^{out}$, or, when a sample shows birefringence, for example. In particular, polarization mode conversion appears if the dielectric tensor of a sample possesses non-vanishing off-diagonal elements. Therefore, in Mueller matrix data from optically isotropic samples, ideally all off-diagonal-block elements vanish, while, for example, magneto-optic birefringence can cause non-zero off-diagonal-block elements in the Mueller matrix.

Here, we define (OHE) data as Mueller matrix data from an (OHE) experiment [Eq. 1] with magnetic field +/−B and the corresponding to the zero field dataset:

$$M_{OHE}^\pm = M(\varepsilon_{B=0} + \varepsilon_{+/-B}) \quad (13)$$

$$\delta M^\pm = M_{OHE}^\pm - M_0 = \Delta M(\varepsilon_{B=0} + \varepsilon_{\pm B}) \quad (14)$$

where $M_0 = M(\varepsilon_{B=0})$ is the Mueller matrix of the zero field experiment, and $\Delta M(\varepsilon_{B=0}; \varepsilon_B)$ is the magnetic field induced change of the Mueller matrix. This form of presentation is in particular advantageous in case the magnetic field causes only small changes in the Mueller matrix, and provides improved sensitivity to magnetic field dependent model parameters during data analysis. Another form of presentation for derived (OHE) data is:

$$\delta M^+ \pm dM^- = \Delta M(\varepsilon_{B=n}; \varepsilon_{+B}) \pm \Delta M(\varepsilon_{B=n}; \varepsilon_{-B}), \quad (15)$$

that can be used to inspect symmetry properties of magneto-optic Mueller matrix data, and can help to improve the sensitivity to magnetic field dependent model parameters during data analysis.

Mueller Matrix Data Acquisition (GE)

Spectroscopic ellipsometers can be categorized according to their polarization optical components and operation principles, where different subsets of Mueller matrix elements may be accessible. For example Spectroscopic ellipsometers can be classified into two categories: (i) polarizer-sample+ rotating analyzer ellipsometers ($PSA_R$) or rotating-polarizer+sample-analyzer ($P_RSA$) configurations, capable of measuring the upper left 3×3 block of the Mueller matrix; and (ii) rotating compensator(s) ellipsometers (RCE) in polarizer-sample-rotating-compensator-analyzer ($PSC_RA$) or polarizer-rotating-compensator-sample-analyzer ($PC_RSA$) configuration, capable of measuring the upper left 3×4 or 4×3 block of the Mueller matrix, respectively.

Mathematically all ellipsometers, can be described by the ordered multiplication of Mueller matrices, corresponding to their consecutive optical elements. The Mueller matrices of a polarizer (P), analyzer (A), compensator (δ) with phase shift, coordinate rotation along beam path (Rθ) by an angle θ, and of the sample (M) are given by:

$$P = A = \frac{1}{2}\begin{bmatrix} 0 & 0 & 1 & 1 \\ 0 & 0 & 1 & 1 \\ 0 & 0 & 0 & 0 \\ 0 & 0 & 0 & 0 \end{bmatrix} \quad R(\theta) = \begin{bmatrix} 1 & 0 & 0 & 0 \\ 0 & \cos(2\theta_j) & \sin(2\theta_j) & 0 \\ 0 & -\sin(2\theta_j) & \cos(2\theta_j) & 0 \\ 0 & 0 & 0 & 1 \end{bmatrix} \quad (16)$$

$$C(\delta) = \begin{bmatrix} 1 & 0 & 0 & 0 \\ 0 & 1 & 0 & 0 \\ 0 & 0 & \cos(\delta) & -\sin(\delta) \\ 0 & 0 & \sin(\delta) & \cos(\delta) \end{bmatrix} \quad M = \begin{bmatrix} M11 & M12 & M13 & M14 \\ M21 & M22 & M23 & M24 \\ M31 & M32 & M33 & M34 \\ M41 & M42 & M43 & M44 \end{bmatrix}$$

respectively. Execution of the matrix multiplication characteristic for the corresponding ellipsometer type shows that, due to the rotation of optical elements, the measured intensity at the detector is typically sinusoidal. Fourier analysis of the detector signal provides Fourier coefficients, which are used to determine the Mueller matrix of the sample.

Data Analysis

Ellipsometry is generally an indirect experimental technique. Therefore, in general, ellipsometric data analysis invokes model calculations to determine physical parameters in dielectric tensors or the thickness of layers, for instance. Sequences of homogeneous layers with smooth and parallel interfaces are assumed in order to calculate the propagation of light through a layered sample, by the 4×4 matrix formalism. To best match the generated data with experimental results, parameters with significance physical model parameter in dielectric tensors, layer thicknesses etc. are varied and Mueller matrix data is calculated for all spectral data points, angles of incidence and magnetic fields. During the mean square error (MSE) regression, the generated Mueller matrix data $M_{i,j,k}^G$ is compared with the experimental Mueller matrix data $M_{i,j,k}^B$ and their match is quantified by the MSE:

$$MSE = \sqrt{\left(\frac{1}{9S-k}\right)\sum_{i=1}^{4}\sum_{j=1}^{4}\sum_{k=1}^{5}\left(\left(M\left(\frac{E}{i,j,k}\right) - M\left(\frac{G}{i,j,k}\right)\right) / 6M\left(\frac{E}{i,j,k}\right)\right)^2}$$

where S, K and $\sigma_{M_{i,j,k}}^G$ denotes the total number of spectral data points, the total number of parameters varied during the non-linear regression process, the number experimentally determined columns and rows of the Mueller matrix and the standard viation of M{I,j,k}, obtained during the experiment, respectively. For fast convergence of the MSE regression, the Levenberg-Marquardt fitting algorithm is used. The MSE regression is interrupted when the decrease in the MSE is smaller than a set threshold and the determined parameters are considered as best model parameters. The sensitivity and possible correlation of the varied parameters is checked and, if necessary, the model is changed and the process is repeated. Eventually values for parameters in the mathematical model of the sample being characterized are arrived at and represent very reliable insight to actual physical values.

It is also mentioned, that is some special cases ellipsometry can provide results that allow direct analytical solutions for such as concentration and mobility of charge carriers based on off diagonal Jones or Mueller Matrix element value slopes, as a function of an applied magnetic field. While the typical approach to determining at least one of the free charge carrier longitudinal and/or transversal effective masses, and/or concentration, and/or mobility and/or type from said anisotropic values for said at least a partial Jones or Mueller Matrix determining involves use of mathematical regression onto a model of the sample and ellipsometer or polarimeter system used to evaluate the Jones or Mueller Matrix elements, it is possible under certain circumstances to arrive at concentration and mobility of carriers by a direct calculation. This is because in the situation wherein the optical path length in a sample, including associated, (eg. Fabry-Perot), cavity forming elements, is a multiple of the wavelength, (ie. Fabry-Perot resonance is achieved, there is a linear relationship between applied magnetic field and slope in Off-diagonal Matrix elements. The slope is different for each of the off-diagonal Matrix elements determined, but in all cases depends only on mobility and concentration of charge carriers. Further, while this determination involves use of slopes in two such off-diagonal Matrix elements as the applied magnetic field is ramped up, it is generally considered that the slope be determined at two such applied magnetic fields. However, as the off-diagonal Matrix elements vanish when the applied magnetic field is zero, a single applied field measurement can sufficient to determine the necessary slopes.

THz Time-Domain Spectroscopy Based Ellipsometry

Beside THz frequency-domain spectroscopy based ellipsometry discussed in this Specification, ellipsometry and magneto-optic ellipsometry can be conducted using THz time-domain spectroscopy (THz-TDS), see Sakai, "Terahertz Optoelectronic" Springer-Verlag, (2005}. Typically THz-TDS is based on the Fourier transformation of the time resolved signal of ultra-short (picosecond) laser pulses, revealing the THz spectrum. THz-TDS was developed in the 1980s, and had had its practical breakthrough in the 1990s. THz-TDS has since been used to study the birefringence of a variety of materials in the THz range, as well as the THz magneto-transmittance for a variety of semiconductors. Polarization sensitive THz magneto-transmittance based on THz-TDS were reported in 1997. THz ellipsometry based on THz-TDS was reported by the Hangyo-group in 2001, Nagashima & Hangyo, (see App. Phys. Lett., 79, 3017, (2001), and Matsumoto et al., J. J. APP. Phys. 48, (2009) and Matsumoto et al., Optics Letters, Vol. 36, No. 2, (Jan. 15, 2011), and in 2012 by Neshat Op. Soc., Vol 20, No. 27, (2012)). THz-TDS magneto-ellipsometry measurements were reported by Ino et al., (see Phys. Rev. B, 70, (2004)), but external magnetic fields were limited to B approximately 0.5 T and Mueller matrix capabilities of the instrument were not demonstrated.

Search of Patents and Published Applications

A Search of the USPTO Database was conducted for the terms "Optical Hall Effect" (OHE) and independently, (1) Ellipsometer, (2) Polarimeter, (3) Terahertz, (4) THz, in both Issued Patent and Published Application categories. No hits were found. When "Optical Hall Effect" was Searched on its own, without an accompanying additional term, many hits were obtained in both categories. However, said hits seem to be referring to "in the alternative" type systems. That is, an invention can use Hall Effect or Optical sensing etc. to arrive at a desired result. While not particularly relevant to the Invention Claimed herein, a few known Patents that describe Terahertz Ellipsometer Systems or the like are U.S. Pat. No. 8,169,611 8,416,408; 8,488,119; 8,705,032 and 8,736,838 to Herzinger or Herzinger et al., and which are assigned to the J.A. Woollam Co. Inc., some in conjunction with the Board of Regents of the University of Nebraska. It is also noted that while the present invention has generally been practiced by the Inventors herein using a Rotating Analyzer Ellipsometer configuration, any Ellipsometer configuration can be applied including Rotating Polarizer or Rotating Compensator, and combinations thereof. As well, Modulation Element Ellipsometers can also be employed and should be considered within the Claims if not otherwise excluded by Claim language. Although not specifically directed to Infrared or Terahertz wavelength ranges, An example of a Patent covering such a Modulation Element configuration is U.S. Pat. No. 5,657,126 to Duchamrme et al.

Finally in this Background Section of the Specification, it is noted that terminology used in the Claims regarding Vacuum Ultraviolet, Mid-Ultraviolet, Near-Ultraviolet, Visible, Near-Infrared, Mid-Infrared, Far-Infrared, (eg. some being examples of Fourier Transform Infrared) and Terahertz wavelength ranges can be roughly defined as:

VUV (eg. 0.01-0.2 um);
MUV (eg. 0.2-0.3 um);
NUV (eg. 0.3-0.4 um);
Visible (eg. 0.4-0.75 um);
NIR; (eg. 0.75-3 um);
MIR; (eg. 3-30 um);
FIR; (eg. 30-350 um); and
THz (eg. 350→1000 um).

The relevant literature is not absolutely consistent in said definitions however and differences in how various publications define said ranges should not be interpreted to be significant in disclosure of the present invention.

For insight, assuming a classical Newtonian equation of motion with Lorentz force contribution due to the presence of an external static magnetic field (i.e., no quantum phenomena), the dielectric function tensor can be expressed as in equation 6 herein, (eg. the Lorentz-Drude model). For the common case of free-charge carriers, we assume no restoring force, thus $w0=0$ (Drude Model). The off-diagonal dielectric function tensor elements which constitute the optical Hall effect (birefringence in the presence of magnetic fields, i.e., non-zero off-diagonal MM elements), show significant contributions only in the spectral ranges where we see free-charge carrier contribution also without magnetic field. Even for highly doped semiconductors those contributions are limited to the long-wavelength range or more precisely to wavelength longer than the visible spectral range. For 2D materials with quantum mechanical effects, we observe resonances in the MM data related to discrete transitions between confined electronic states (so-called Landau level transitions). Even in materials with extremely high mobility such as graphene, at ultra-low temperature of 1.5K, and with strong magnetic field of 8T, observable transitions in the MM data are limited to wavelengths longer than 3 um.

It is also pointed out that even though possible effects might not be governed by the exact same equations as in the IR spectral range, there might still be magnetic field induced effects in the UV and VUV spectral range described by a different dielectric function tensor.

A recent article by Knight et al. titled "In Situ Terahertz optical Hall Effect Measurement of Ambient Effects on Free Charge Carrier Properties of Epitaxial Graphene", Scientific Reports 7:5151, Jul. 11, 2017 is identified. This article demonstrates how the atmospheric content at the surface of epitaxial graphene can have effects, observable in Mueller Matrix Elements related to free charge carrier properties.

Even in view of the prior art, need remains for improved systems and methods of their use that allow the Optical Hall Effect (OHE) to be monitored at room temperature and relatively low Tesla field strengths provided by small permanent magnets.

DISCLOSURE OF THE INVENTION

The present invention is a method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:

a) providing an ellipsometer comprising:
  a source of a beam of electromagnetic radiation characterized by at least one wavelength in a selection from the group consisting of the:
    Vacuum Ultraviolet;
    Near-Ultraviolet;
    Mid-Ultraviolet;
    Visible;
    NIR;
    MIR;
    FIR; and
    THz ranges;
  a polarizer;
  a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s), said stage being present inside a chamber that comprises at least one selection from the group consisting of:
    at least an input port for use in controlling the atmospheric content and pressure inside said chamber; and
    a temperature controller inside said chamber;
  an analyzer; and
  a detector of relevant electromagnetic radiation wavelengths; and
  further providing a source of a magnetic field;
b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;

c) setting at least one of the temperature and/or atmospheric content and pressure thereof inside said chamber;

d) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;

e) from data accumulated by said detector with the system adjusted as described in steps b) and c), evaluating anisotropic values for at least a partial Jones or Mueller Matrix; and f) from said anisotropic values for said at least a partial Jones or Mueller Matrix determining at least one of the free charge carrier longitudinal and/or transversal effective masses, and/or concentration, and/or mobility and/or type.

Said method is characterized in that it comprises at least one selection from the group consisting of a1')-a7'), directly following:

a1') data is accumulated with the source provided beam of electromagnetic radiation set so that it provides at least one substantially exact multiple of an optical path length within said sample;

a2') nine Mueller Matrix are evaluated, said nine elements being M11, M12, M13, M21, M22, M23, M31, M32 and M33, and wherein each Mueller Matrix elements M12, M13, M21, M22, M23, M31, M32 and M33 is divided by the value of M11 prior to use in evaluating free charge carrier longitudinal and transversal effective masses, concentration, mobility and type;

a3') at least a partial Mueller matrix is determined and, of the Mueller Matrix elements M11, M12, M13, M21, M22, M23, M31, M32 and M33 that can be determined, at least M11, and at least one of M23 and M32 are, said approach to determining values for M11, and at least one of M23 and M32 being distinguished in that data is determined by a selection from the group consisting of:

placing said sample on said stage for supporting a sample with the back side thereof in contact with said stage and obtaining a first set of data, then flipping said sample so that it's surface is in contact with said stage and obtaining a second set of data; and first placing the north pole of a permanent magnet near to the sample and obtaining a first set of data, and then placing the south pole of the same or another magnet so that the south pole thereof is near the sample and obtaining a second set of data, followed by subtracting said second set of data from said first, or vice-versa, for each of the resulting M11, and at least one of said resulting M23 and M32 Mueller Matrix elements determined, and wherein each determined M23 and M32 is divided by M11, prior to using said resulting at least one of M23 and M32 values as data upon which to regress a model of said sample that includes free charge carrier longitudinal and transversal effective masses, concentration, mobility and type, thereby allowing their evaluation;

a4') at least one of M13 and M3 is determined in addition to M11 by the procedure of obtaining a first set of data with the sample back side in contact with said stage and then flipping said sample or over so that it's surface is in contact with said stage and obtaining a second set of data; or by first placing the north pole of a permanent magnet near to the sample and obtaining a first set of data, and then placing the south pole of the same or another magnet so that the it is near the sample and obtaining a second set of data;

and then subtracting said second set of data from said first, or vice-versa, for each of the resulting M11, and at least one of said resulting M13 and M31 Mueller Matrix elements determined, prior to using said resulting at least one of M23 and M32 and at least one of M13 and M31 values as data upon which to simultaneously regress a model of said sample that includes free charge carrier longitudinal and transversal effective masses, concentration, mobility and type, thereby allowing their evaluation;

a5') at least a partial Mueller matrix is determined and, of the Mueller Matrix elements M11, M12, M13, M21, M22, M23, M31, M32 and M33 that can be determined, at least M11, and at least one of M13 and M31 are, said approach to determining values for M11, and at least one of M13 and M31 being distinguished in that data is determined by a selection from the group consisting of:

placing said sample on said stage for supporting a sample with the back side thereof in contact with said stage and obtaining a first set of data, then flipping said sample so that it's surface is in contact with said stage and obtaining a second set of data; and by first placing the north pole of a permanent magnet near to the sample and obtaining a first set of data, and then placing the south pole of the same or another permanent magnet so that is near the sample and obtaining a second set of data;

and then subtracting said second set of data from said first, or vice-versa, for each of the resulting M11, and at least one of said resulting M23 and M32 Mueller Matrix elements determined, and wherein each determined M13 and M31 is divided by M11, prior to using said resulting at least one of M13 and M31 values as data upon which to regress a model of said sample that includes free charge carrier longitudinal and transversal effective masses, concentration, mobility and type, thereby allowing their evaluation;

a6') at least one of M32 and M23 is determined in addition to M11 by the procedure of data being determined by obtaining a first set of data with the sample back side in contact with said stage and then flipping said sample over so that it's surface is in contact with said stage and obtaining a second set of data; or by first placing the north pole of a permanent magnet near to the sample and obtaining a first set of data, and then placing the south pole of the same or another permanent magnet so that is near the sample and obtaining a second set of data, and then subtracting said second set of data from said first for each of the resulting M11, and at least one of said resulting M23 and M32 Mueller Matrix elements determined, prior to using said resulting at least one of the M23 and M32 and at least one of M23 and M32 values as data upon which to simultaneously regress a model of said sample that includes free charge carrier longitudinal and transversal effective masses, concentration, mobility and type, thereby allowing their evaluation;

a7') Mueller Matrix element M11, and at least one selection from the group of elements consisting of M12, M13, M23, or at least one selection from the group of elements consisting of M12, M13, M33 is evaluated by, for each selection, a selection from the group consisting of:

first placing said sample on said stage for supporting a sample with the back side thereof in contact with said stage and obtaining a first set of data, and second flipping said sample so that it's surface is in contact with said stage and obtaining a second set of data; and by first placing the north pole of a permanent magnet near to the sample and obtaining a first set of data, and second placing the south pole of the same or another magnet so that it is near the sample and obtaining a second set of data;

followed by subtracting the first from the second or the second from the first obtained set of data for each selection from the group of elements consisting of at least one selection from the group consisting of M12, M13, M23, or at least one selection from the group of elements consisting of M12, M13, M33;

followed by dividing said result(s) by M11, before, from said anisotropic value(s), determining at least one of the free charge carrier concentration and/or mobility.

For breadth and additional insight, previously, in Parent application Ser. No. 14/545,816, the invention was described as, comprising a (still valid in this CIP) method of evaluating at least some of the free charge carrier longitudinal and/or transversal effective mass(es) and/or concentration and/or mobility and/or free charge carrier type in a sample having a back side and a surface. Said sample can be transparent or semi-transparent, (or even approaching substantially opaque beyond a distance from a surface thereinto at wavelength(s) utilized where a detector signal enhancing cavity effect is not required to be utilized). Said method comprises the steps of:
  a) providing an ellipsometer comprising:
    a source of a beam of electromagnetic radiation characterized by at least one wavelength in a selection from the group consisting of the:
      Vacuum Ultraviolet;
      Near-Ultraviolet;
      Mid-Ultraviolet;
      Visible;
      NIR;
      MIR;
      FIR; and
      THz ranges;
    a polarizer;
    a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s);
    an analyzer; and
    a detector of relevant electromagnetic radiation wavelengths.
  Said method further comprises providing a source of a magnetic field.
Said method further comprises:
  b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;
  c) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data.

Said method then continues with:
  d) from data accumulated by said detector with the system adjusted as described in steps b) and c), evaluating anisotropic values for at least a partial Jones or Mueller Matrix; and
  e) from said anisotropic values for said at least a partial Jones or Mueller Matrix determining at least one of the free charge carrier longitudinal and/or transversal effective masses, and/or concentration, and/or mobility and/or type.

Said method can involve evaluation of said free charge carrier longitudinal and/or transversal effective masses and/or concentration and/or mobility and/or type is determined based on data acquired when the interaction of said electromagnetic beam of electromagnetic radiation with said sample involves transmission thereof through said sample which is transparent or semi-transparent, (eg. $<10^{16}$ cm$^{-3}$ doping in Silicon), at wavelength(s) utilized. Said method can also involve that data used in evaluation of said longitudinal and/or transversal effective masses and/or concentration and/or mobility and/or type is determined based on data acquired when the interaction of said electromagnetic beam of electromagnetic radiation with said sample involves reflection thereof from said sample which is even approaching substantially opaque beyond a distance thereinto from a surface thereof at wavelength(s) utilized, when a detector signal enhancing effect is not practiced.

Said method can involve said polarizer being set to at least one additional polarization setting and/or wherein said source of a magnetic field set to at least one additional magnitude and/or a different wavelength of electromagnetic radiation different from that originally utilized is utilized, and additional data is accumulated by said detector, which additional data is also used in evaluation said free charge carrier longitudinal and/or transversal effective masses and/or concentration and/or mobility and/or type.

Said method can involve data being accumulated with the source provided beam of electromagnetic radiation set so that it provides at least one substantially exact multiple of an optical path length within said sample.

Said method can involve the source of said magnetic field is a permanent magnet that provides a magnetic field of about 1 T, or less at the sample surface. It is further within the scope of the present invention to apply a small electromagnet of a similar Tesla (T) strength in place of, or in addition to the permanent magnet, but this begins to move away from a benefit of the present invention, that benefit being the ability to acquire good data with inexpensive easy to use small, (eg. 0.1-0.5 T or more), permanent magnets.

Said method can involve the sample being transparent or semi-transparent at wavelength(s) utilized, in which said source of said magnetic field is a permanent magnet, and wherein a gap exists between an associated surface thereof from which a magnetic field other than parallel thereto at said sample surface emanates, and a backside of said sample.

Said method can involve that the beam of electromagnetic radiation interacts with the sample by at least partially transmitting through it and in which the stage tip and/or tilt is determined based primarily on setting a desired gap geometry between a surface associated with said source of magnetic field and the backside of said sample, said desired gap, after being determined being secured in place. Said method then can continue with said stage tip and/or tilt being secondarily set to provide an angle-of-incidence and/or plane-of-incidence at which said beam of electromagnetic radiation approaches the surface of said sample. It is noted that the associated surface of said magnet can be of the magnet per se. or can be an added element that presents and effective surface from which a magnetic field emanates. Stated otherwise, the present invention methodology provides that it is convenient to do a primary tip/tilt to set a desired gap geometry between a surface associated with said source of magnetic field and the backside of said sample, and then fix said orientational relationship, followed by performing an additional, secondary, tip/tilt alignment to set the desired angle-of-incidence and/or plane-of-incidence at which said ellipsometer beam of electromagnetic radiation approaches the surface of said sample.

Said method can, however, involve the beam of electromagnetic radiation interacting with the sample by reflecting therefrom and in which the stage tip and/or tilt is determined based primarily on orienting the surface of said sample so that the beam of electromagnetic radiation approaches said sample surface at a desired angle-of-incidence and/or plane-of-incidence without attention to configuring a gap as alluded to above.

Said methodology can involve determining nine elements of the Mueller Matrix being evaluated, said nine elements being M11, M12, M13, M21, M22, M23, M31, M32 and M33. Further, said Mueller Matrix elements M12, M13, M21, M22, M23, M31, M32 and M33 can each be divided by the value of M11 prior to use in evaluating free charge carrier longitudinal and transversal effective masses, concentration, mobility and type. Of course this is not a limitation of the invention, and more or less than nine can be determined.

A modified recitation of a present invention method of determining at least some of the free charge carrier concentration and/or mobility in a sample, said sample having a back side and a surface and being transparent or semi-transparent (or even approaching substantially opaque beyond some distance thereinto from a surface thereof when a detector enhancing cavity effect is not utilized), at wavelength(s) utilized, comprises the steps of:

a) providing an ellipsometer comprising:
  a source of a beam of electromagnetic radiation characterized by at least one wavelength in a selection from the group consisting of the:
  Vacuum Ultraviolet;
  Near-Ultraviolet;
  Mid-Ultraviolet;
  Visible;
  NIR;
  MIR;
  FIR; and
  THz ranges.
Said ellipsometer system further comprises:
  a polarizer;
  a stage for supporting a sample, said stage comprising an adjustable surface that is capable of orienting a surface of a sample placed thereupon via adjustment of at least one selection from the group consisting of: stage tip, stage tilt and rotation thereof about an axis projecting substantially normal to said stage surface, to desired value(s); and
  a detector of relevant electromagnetic radiation wavelengths;
and
  further providing a source of a magnetic field.
Said method continues with:
b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;

c) while applying the source of a magnetic field to apply a selected magnitude magnetic field other than parallel thereto at the surface of said sample, causing said source of electromagnetic radiation to provide a beam of electromagnetic radiation comprising at least one wavelength of a substantially exact multiple of a an optical path length in said sample, and which beam is caused to pass through said polarizer and assume a polarization state, interact with said sample, pass through said analyzer and enter said detector, which detector produces sample characterizing data;

d) from data accumulated by said detector with the system adjusted as described in steps b) and c), evaluating anisotropic values for at least a partial Jones or Mueller Matrix; and e) from said anisotropic values for said at least a partial Jones or Mueller Matrix determining at least one of the free charge carrier concentration and/or mobility by direct calculation rather than by a mathematical regression procedure.

The above described methodology can involve using a stage for supporting a sample that functionally comprises:
a) an interface plate comprising said sample supporting stage;
b) a magnetic casing plate for positioning at least one magnet with respect to said sample supporting stage, through which said magnetic casing plate said interface plate projects.
Importantly, said stage for supporting a sample further comprises:
c) a mechanism for adjusting the tip and/or tilt of said stage with respect to a surface associated with said at least one magnet such that said surface associated with said at least one magnet is substantially parallel to the back of a sample placed on said sample supporting stage.

In use said stage for supporting a sample can provide that the magnetic casing plate and interface plate are offset from one another to provide a gap therebetween, which gap contributes to formation of a cavity effect wherein at least some electromagnetic radiation directed at said sample by said source of a beam thereof passes through said sample, reflects from said surface associated with said at least one magnet and re-enters said sample.

Said magnetic casing plate can comprise two magnet holders optionally interconnected by a magnetic material, (eg. iron), support bar.

It is to be understood that the present invention also includes the stage per se. for supporting a sample having a back side and a surface as just described above, and which comprises:
a) an interface plate comprising a sample supporting stage;
b) a magnetic casing plate for positioning at least one magnet with respect to said sample supporting stage;
c) a mechanism for adjusting the tip and/or tilt of said stage with respect to a surface associated with said at least one magnet, such that said surface associated with said at least one magnet is substantially parallel to the back side of a sample placed on said sample supporting stage; such that in use said magnetic casing plate and interface plate are offset from one another and adjusted by said mechanism for adjusting the tip and/or tilt of said stage to provide a gap therebetween that establishes a resonance cavity in which at least some electromagnetic radiation caused to be incident on the sample surface transmits through said sample and reflects from said surface associated with said magnet back into said sample. Said stage further comprises a mechanism for fixing the described relationship between said magnetic casing plate and interface plate, and then allowing the tip/tilt capability be used to adjust an ellipsometer beam angle and/or plane of incidence thereto.

Said stage can be characterized by at least one selection from the group consisting of:

a) said magnetic casing plate comprises two magnet holders, optionally interconnected by a magnetic material support bar;

b) said gap is set by a mechanism, (eg. a motor, typically a computer driven stepper motor), that adjusts the relative orientation between said magnetic casing plate and said interface plate;

c) said gap is formed by placing spacer material between the back of said sample and a surface of said stage upon which said sample is placed;

d) said gap is formed by at a spacer comprising at least one layer of tape between the back of said sample and a surface of said stage upon which said sample is placed.

Another modified recitation of present invention methodology for determining at least one of the free charge carrier concentration and/or mobility in a sample, said sample having a back side and a surface and being transparent or semi-transparent or substantially opaque at some distance thereinto from a surface thereof, (when a detector signal enhancing cavity effect is not utilized), thereinto at wavelength(s) utilized, said method comprising the steps of:

a) providing an ellipsometer comprising:
   a source of a beam of electromagnetic radiation characterized by at least one wavelength selected from the group consisting of: Vacuum Ultraviolet; Near-Ultraviolet;
   Mid-Ultraviolet;
   Visible;
   NIR;
   MIR;
   FIR; and
   THz ranges ranges;
   a polarizer;
   a stage for supporting a sample;
   an analyzer; and
   a detector.

Said methodology continues with:

b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample, and/or adjusting the source of a magnetic field which is oriented to provide a magnetic field other than parallel thereto at said surface of said sample, to achieve a desired value of magnetic field at said sample surface, c) while applying the source of a magnetic field to provide a selected magnitude magnetic field other than parallel thereto at the surface of said sample, causing said source of electromagnetic radiation to provide a beam of electromagnetic radiation which is caused to pass through said polarizer and assume a polarization state, interact with said sample, pass through said analyzer and enter said detector, which detector produces sample characterizing data;

And said method further involves:

d) from data accumulated by said detector with the system adjusted as described in steps b) and c), evaluating anisotropic values for at least a partial Jones or Mueller Matrix; and e) from said values for said at least a partial Jones or Mueller Matrix determining at least one of the free charge carrier concentration and/or mobility.

In any of the present invention methodology the data can be acquired at room temperature. This is a benefit over prior art approaches which require temperatures such as achieved by applying liquid helium.

Further, in any present invention methodology the ellipsometer can further comprise at least one compensator between the source of a beam of electromagnetic radiation and the detector. (It is noted that the presence thereof enables acquiring sufficient data to arrive at a full sixteen (16) member Mueller matrix).

As alluded to, said methodology as recited above involves at least a partial Mueller matrix being determined and, of the Mueller Matrix elements M11, M12, M13, M21, M22, M23, M31, M32 and M33 that can be determined, at least M11, and at least one of M23 and M32 are. Said approach to determining values for M11 and at least one of M23 and M32 can be distinguished in that data is determined by a selection from the group consisting of:

placing said sample on said stage for supporting a sample with the back side thereof in contact with said stage and obtaining a first set of data, then flipping said sample so that it's surface is in contact with said stage and obtaining a second set of data; and first placing the north pole of a permanent magnet near to the sample and obtaining a first set of data, and then placing a south pole of the same or another magnet so that it is near the sample and obtaining a second set of data, which is followed by subtracting said second set of data from said first, or vice-versa, for each of the resulting M11, and at least one of said resulting M23 and M32 Mueller Matrix elements determined, and wherein each determined M23 and M32 is divided by the resulting M11, prior to using said resulting at least one of the resulting M23 and M32 values as data upon which to regress a model of said sample that includes free charge carrier longitudinal and transversal effective masses, concentration, mobility and type, thereby allowing their evaluation.

Said methodology and can further involve at least one of M13 and M31 also being determined by the same procedure of obtaining a first set of data with the sample back side in contact with said stage and then flipping said sample over so that it's surface is in contact with said stage and obtaining a second set of data; or by first placing the north pole of a permanent magnet near to the sample and obtaining a first set of data, and then placing a south pole of the same or another permanent magnet so that it is near the sample and obtaining a second set of data.

As before, the method continues with subtracting said second set of data from said first, or vice-versa, for each of the resulting M11, and at least one of said resulting M13 and M31 Mueller Matrix elements determined, prior to using said resulting at least one of M23 and M32 and at least one of M13 and M31 values as data upon which to simultaneously regress a model of said sample that includes free charge carrier longitudinal and transversal effective masses, concentration, mobility and type, thereby allowing their evaluation.

Likewise, at least a partial Mueller matrix can determined and, of the Mueller Matrix elements M11, M12, M13, M21, M22, M23, M31, M32 and M33 that can be determined, at least M11, and at least one of M13 and M31 are. Said approach to determining values for M11, and at least one of M13 and M31 is distinguished in that data is determined by a selection from the group consisting of:

placing said sample on said stage for supporting a sample with the back side thereof in contact with said stage and obtaining a first set of data, then flipping said sample so that it's surface is in contact with said stage and obtaining a second set of data; and by first placing the north pole of a permanent magnet near to the sample and obtaining a first set of data, and then placing the south pole of the same or another magnet so that it is near the sample and obtaining a second set of data. (Note, where a single permanent magnet is used this amounts to "flipping" it over. However, any approach to modulating the effective magnetic field "seen" by a sample between the obtaining of data sets is within the scope of the present invention. That is, specific examples given are not to be considered to be of a limiting nature as regards the actual motion practiced. Because it is convenient, a preferred approach might involve that a single magnet be literally "flipped" over to cause a change from a North to South pole being closer to a sample, or vice versa, is practiced between acquiring the identified two data sets. It is also possible though, to place two magnets on a slider, one with a North pole and one with a South pole oriented so that they can be made to face toward the sample in use. A lateral sliding motion of said slider then places one and then the other of said north and south poles nearer the sample between acquiring two different data sets. Any configuration which allows a modulation, (not even necessarily a complete pole type change), of a magnetic B Field near a sample is to be considered within the scope of possibilities as regards how to arrive at two data sets, (or modulate a signal).

Said methodology then involves subtracting said second set of data from said first, or vice-versa, for each of the resulting M11, and at least one of said resulting M23 and M32 Mueller Matrix elements determined, and wherein each determined M13 and M31 is divided by M11, prior to using said resulting at least one of M13 and M31 values as data upon which to regress a model of said sample that includes free charge carrier longitudinal and transversal effective masses, concentration, mobility and type, thereby allowing their evaluation.

Further, said methodology can involve at least one of M23 and M32 also being determined by the same procedure of data being determined by the same procedure of data being determined by obtaining a first set of data with the sample back side in contact with said stage and then flipping said sample over so that it's surface is in contact with said stage and obtaining a second set of data; or again by first placing the north pole of a permanent magnet near to the sample and obtaining a first set of data, and then flipping the magnet so that the south pole thereof is near the sample and obtaining a second set of data, and then subtracting said second set of data from said first for each of the resulting M11, and at least one of said resulting M23 and M32 Mueller Matrix elements determined, prior to using said resulting at least one of M23 and M32 and at least one of M23 and M32 values as data upon which to simultaneously regress a model of said sample that includes free charge carrier longitudinal and transversal effective masses, concentration, mobility and type, thereby allowing their evaluation.

Said methodology can involve the sample supporting stage being adjusted to be at a desired distance from a magnet, by placing at least one layer of spacer material, (eg. Tape), between said sample supporting stage and the sample supported thereby, or by use of a motor to achieve a desired cavity gap. Any approach to achieving a desired cavity gap geometry, however is within the scope of the present invention.

It is noted that the foregoing methodology can involve that the permanent magnet utilized provides a field strength at the sample of between 0.1-0.5 or more Tesla.

Another recitation of present the invention methodology of enhancing the capability of determining free charge carrier concentration and mobility in a sample having a back side and a surface, said sample being transparent or semi-transparent at wavelength(s) utilized, said method comprising the steps of:

a) providing an ellipsometer comprising:
   a source of a beam of electromagnetic radiation characterized by at least one wavelength in a selection from the group consisting of the: Vacuum Ultraviolet;
   Near-Ultraviolet;
   Mid-Ultraviolet;
   Visible;
   NIR;
   MIR;
   FIR; and
   THz ranges;
   a polarizer;
   a stage for supporting a sample;
   an analyzer; and
   a detector;
   and a source of a magnetic field having a surface associated therewith and which is oriented to provide a magnetic field other than parallel thereto at said surface of said sample.

As before, said method continues with:

b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample, and/or further adjusting the source of a magnetic field so that it is oriented to provide a magnetic field other than parallel thereto at said surface of said sample of a desired value;

c) while applying the source of a magnetic field to apply a magnetic field other than parallel thereto at the surface of said sample or a desired value, causing said source of electromagnetic radiation to provide a beam of electromagnetic radiation comprising at least one wavelength of substantially an exact multiple of an optical path length in said sample, which beam is caused to pass through said polarizer and assume a polarization state, interact with said sample, pass through said analyzer and enter said detector, which detector produces sample characterizing data.

Said method then further involves:

d) from data accumulated by said detector with the system adjusted as described in steps b) and c), evaluating anisotropic values for at least a partial Jones or Mueller Matrix; and e) from said values for said at least a partial Jones or Mueller Matrix directly determining at least one of the free charge carrier concentration and/or mobility.

Said just recited methodology is, however, distinguished in that, while data is being accumulated by said detector, a gap is caused to exist between at least one selection from the group consisting of:
1) said sample backside and the sample supporting stage; and
2) said sample supporting stage and said surface associated with said source of a magnetic field which is oriented to provide a magnetic field other than parallel thereto at said surface of said sample of a desired value;
such that a cavity is formed in which at least some electromagnetic radiation in the beam thereof directed at said sample by said source of a beam of electromagnetic radiation passes through said sample, and is coherently reflected back thereinto by said surface associated with said source of a magnetic field.

Said just recited methodology can involve the gap being caused to exist by placing spacer material between said sample back side and said sample supporting stage, and/or in which the gap is caused to exist by, for instance, application of, for instance, a motor applied between an interface plate that comprises said sample supporting stage, and a magnet casing plate that comprises said surface associated with said source of a magnetic field which is oriented to provide a magnetic field other than parallel thereto at said surface of said sample.

In any of the recited methodology the polarizer can be a rotatable polarizer and the analyzer can be a rotating analyzer.

In any of the recited methodology the magnetic field which is applied other than parallel thereto at the surface of said sample can preferably applied substantially, or exactly perpendicular to said sample surface. This preference is not limiting however.

As mentioned earlier, the methodology can further comprise providing a compensator between said source and detector to increase the capability of determining more complete Mueller matrix element determining data.

In most applications of practicing present invention methodology mathematical regression is applied to Jones or Mueller matrix elements to arrive at the desired values, however, in some special cases direct mathematical calculation to Jones or Mueller matrix elements can be practiced to arrive at the desired values for concentration and/or mobility of charge carriers present.

As it is important to be clear regarding present invention ellipsometer or the like systems that can be applied in practice of the present invention methodology, it is here presented that such systems comprise:
  a polarization state generator;
  a stage for supporting a sample, said stage having a substantially flat surface; and
  a polarization state detector.
(Note, the terminology "polarization state generator" refers to what proceeds a sample and sets a polarization state in a beam of electromagnetic radiation caused to impinge on a sample at an angle-of-incidence and plane-of-incidence values, and "polarization state detector" refers to follows a sample and serves to develop data based on electromagnetic radiation entering thereinto).
Continuing, in use said polarization state generator is caused to direct a polarized beam of electromagnetic radiation to interact with a sample on said stage for supporting a sample, which after said interaction presents as a beam of electromagnetic radiation that enters said polarization state detector, that in response produces sample characterizing data.

Importantly, to stress the importance of the point, it is again noted that said just recited present invention ellipsometer or the like system is distinguished in that said stage for supporting a sample is functionally a part of a cavity that directs electromagnetic radiation that passes through a transparent or semi-transparent sample supported upon said stage having a substantially flat surface to be reflected back into said transparent or semi-transparent sample, such that when sample characterizing data is being accumulated by said polarization state detector, it is enhanced over what it would be otherwise as a result of coherent interaction in said transparent or semi-transparent sample between electromagnetic radiation incident thereupon provided by said polarization state generator, and electromagnetic radiation that reflects back into said transparent or semi-transparent sample as a result of said resonance effect, a resulting coherent combination of said two identified contributions of electromagnetic radiation in said sample then comprising said beam that enters said polarization state detector.

Said system as just recited can further comprise a magnet casing plate, such that in use a magnet can be secured thereto in a manner such that a magnetic field directed other than parallel thereto at the sample surface is presented to said sample, and which magnet casing plate and substantially flat surface associated with said magnet can be adjusted to be substantially parallel thereto at said substantially flat surface of said stage.

And, said system as just recited can further comprise a mechanism that enables aligning the substantially flat surface of said stage and the substantially flat surface associated with said magnet so that they are substantially parallel to one another by a tip/tilt procedure. Said present invention provides that it can be said stage for supporting a sample that is caused to undergo said tip/tilt procedure to align the substantially flat surface associated with said magnet substantially parallel to the stage substantially flat surface, and/or it can be said substantially flat surface associated with said magnet that is caused to undergo said tip/tilt procedure to align the substantially flat surface associated with said magnet substantially parallel to the stage substantially flat surface.

In use said system as just described can provide that said substantially flat surface associated with said magnet is caused to be aligned substantially parallel to the stage substantially flat surface, then said resulting orientation is secured in place, followed by said tip/tilt procedure being practiced primarily to align said stage substantially flat surface so that desired angle-of-incidence and/or plane-of-incidence of said beam of electromagnetic radiation caused to be directed at said sample by said polarization state generator, is/are achieved. This provides insight as to how the inventors have used the described system to achieve results.

It is also noted that said system can be characterized in that the resonance effect is enhanced by placing spacer material between the stage for supporting a sample and a sample supported thereby.

It is further noted that while the resonance cavity effect is not easily achieved for samples which are effectively opaque below some distance from the sample surface, (eg. 50 microns is to be considered a typical distance), the described system can still be applied allow sample investigation within said typical 50 microns via a beam of electromagnetic radiation which is caused to reflectively interact with a sample surface, to produce sample characterizing data. It is also noted that where sample characterizing data is obtained without use of data enhancing cavity effects, samples analyzed can be transparent, semi-transparent or even opaque below some distance into said sample from a surface thereof. The later situation requires that reflective electromagnetic beam and sample interaction be applied of course, as a beam cannot transmit through a sample with is opaque at wavelengths used. This is not a limitation where transparent or semi-transparent sample are analyzed at wavelengths utilized. Note, different wavelengths provide different characteristics as regards if a sample is generally "transparent" or "semi-transparent". This is especially true for semiconductors. Therefore selection of an appropriate wavelength in the Visible, Mid-Infrared, Far Infrared or THz range is important where cavity data enhancement effects are to be utilized. It is emphasized that this comprises a major benefit provided by the present invention. Electromagnetic radiation transmitted through and reflected back into a sample provides significant benefits. Further, it is to be understood that a present invention reference to wavelength(s) being "at least one substantially exact multiple of an optical path length in a sample" is to be interpreted wherein said wavelength(s) is/are determined when a sample is in a cavity, which cavity geometry affects what the wavelength(s) is/are. That is, for the purposes of the present invention the term "sample" is to be considered in the context of the cavity of which it is a part and it is the whole thereof that is defining of said wavelength(s). This should be kept in mind while considering Claim language. And, while opaque samples can be analyzed according to the teachings herein in reflection mode, data enhancing resonance effects are practical only where a sample is at least semi-transparent.

In view of the foregoing, it is considered that there are many Patentable aspects of the present invention, but in particular it is believed that use of a cavity to reflect electromagnetic radiation back into a transparent or semi-transparent sample after it passes therethrough, for the purpose of enhancing an ellipsometer beam signal that enters an ellipsometer system detector, especially in combination with use of a small, (eg. 0.1-0.5 T or more, but usually <1.0), permanent magnet to provide a B Field at a sample surface to investigate a sample via Optical Hall Effect methodology, provides new, non-obvious and useful invention.

It is further mentioned that the use of a cavity to reflect electromagnetic radiation back into a transparent or semi-transparent sample after it passes therethrough, for the purpose of enhancing an ellipsometer beam signal that enters an ellipsometer system detector, is applicable to use in any ellipsometer or polarimeter or the like systems even when the Optical Hall Effect is not being investigated. That is, operation of any ellipsometer or polarimeter or the like system can be enhanced by application of a reflecting cavity.

Further, such a cavity can be modulated as regards its size, (eg. depth), during sample investigation and thereby modulate the signal the ellipsometer or the like system detector receives. This allows for instance, while not a requirement, an ellipsometer or polarimeter or the like, polarizer and analyzer to remain fixed during data acquisition while still deriving the benefits of a modulated beam.

For insight, unraveling the doping-related charge carrier scattering mechanisms in two-dimensional materials such as graphene is vital for limiting parasitic electrical conductivity losses in future electronic applications. While electric field doping is well understood, assessment of mobility and carrier density as a function of chemical doping remained a challenge thus far. The contact-less OHE technique can be utilized to study sheet concentration, type, effective mass, and mobility of free-charge carriers in 2d materials in-situ while exposing the sample surface to specific gas environments." Further, the purpose of changing temperature of a sample is to study scattering mechanisms in the sample: different scattering types have different temperature dependence. Generally, scattering is smallest at low temps, i.e. mobility is highest and a stronger OHE signal can be detected at same magnetic field strength.

Finally, a more broadly stated present invention method allows for, but does not require the stage to be present in a chamber for controlling atmosphere or temperature, but is otherwise substantially similar to the methodology recited above. It is however characterized in that at least some elements of a full Mueller Matrix are evaluated, said elements being M11, M12, M13, M14, M21, M22, M23, M23, M24, M31, M32 and M33, M34, M41, M42, M43 and M44, and wherein each Mueller Matrix element is divided by a normalizing factor prior to use in evaluating free charge carrier longitudinal and transversal effective masses, concentration, mobility and type. The normalizing factor need can, but need not be matrix element M11. In particular, the at least one off-diagonal Mueller matrix element evaluated can be selected from the group consisting of: M14, M24, M41 and M4, as well as the other matrix element earlier described herein.

The invention will be better understood by reference to the Detailed Description Section of this Disclosure, in combination with the Drawings.

BRIEF DESCRIPTION OF THE DRAWINGS

FIG. 1D provides a reference for a general THz based ellipsometer system.

FIGS. 1D', 1D" and 1D'" show demonstrative systems for placing magnets near a sample stage as in FIG. 1D.

FIG. 1E shows another embodiment of a THz ellipsometer system developed by the J.A. Woollam Co.

FIG. 1E' demonstrates that the stage in FIG. 1E can be rotated to affect an angle of incidence of a beam of electromagnetic radiation there-approaching.

FIG. 4C shows a 4×4 Mueller Matrix.

DETAILED DESCRIPTION

Figure 1A:
FIG. 1A shows a block diagram of an integrated VIS-MIR and FIR-THz (OHE) instrument.

Turning now to FIG. 1A there is shown a block diagram of an integrated VIS-MIR and FIR-THz (OHE) instrument. Said integrated (OHE) instrument contains multiple light sources and detectors, and covers a spectral range from 3 $cm^{-1}$ to 7000 $cm^{-1}$ (0.1-210 THz or 0.4-870 meV). It is noted that both ellipsometer sub-systems can be operated without the magneto-cryostat sub-system (MCS) in a variable angle of incidence ellipsometry mode. The angle of incidence is defined as the angle between the surface normal of the sample and the incoming beam.

The present invention, in its preferred embodiment, is an integrated 1A VIS-MIR and FIR-THz (OHE) instrument as identified in FIG. 1A, however said preferred embodiment is suitable for use at room temperature and B fields produced by relatively small permanent magnet(s) in an equivalent to the (MCS) subsystem which will be described with respect to FIGS. 2A-2E.

Figure 1C:
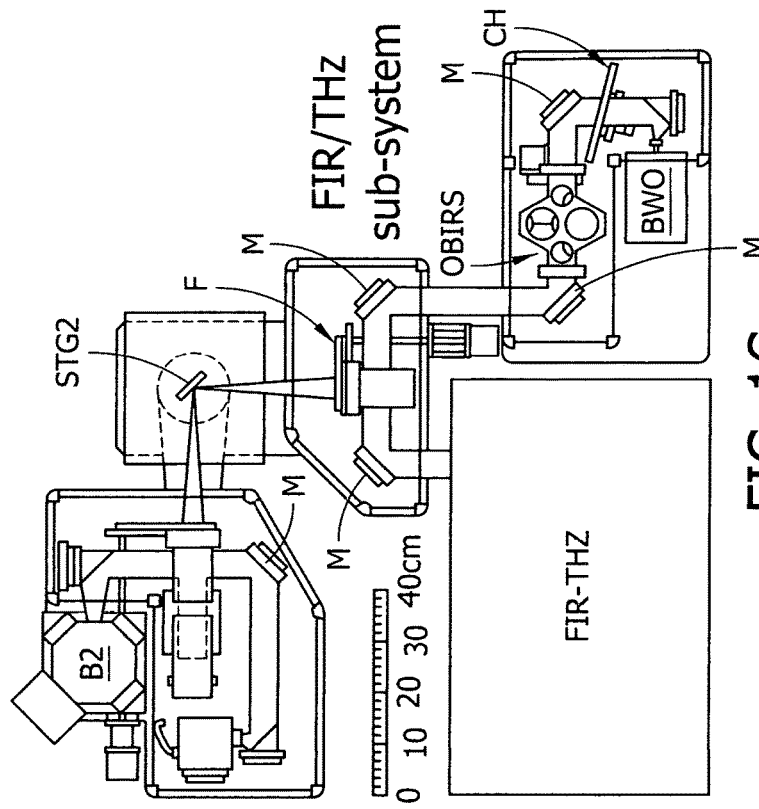
FIGS. 1B and 1C show the VIS-MIR and FIR-THz subsystems in more detail.
Figure 1B:
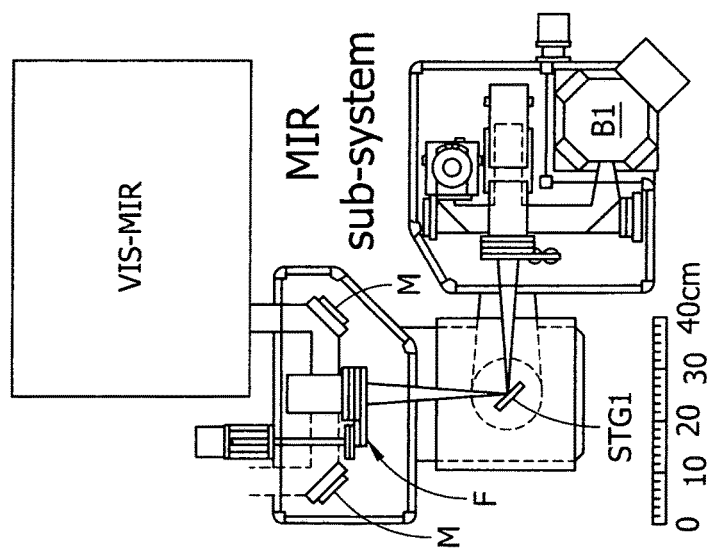

Continuing, FIGS. 1B and 1C show the VIS-MIR and FIR-THz subsystems in more detail.

FIG. 1D provides a reference for a general THz based ellipsometer system, showing:
  a source (BWO) of terahertz electromagnetic radiation;
  a first rotatable polarizer (WGP1);
  a first rotatable element (RE1);
  a stage (STG) for supporting a sample (S);
  a second rotatable element (RE2);
  a second rotatable polarizer (WGP2); and
  a detector (DET) of terahertz electromagnetic radiation.

It should be appreciated that a combination of a source (BWO) of terahertz electromagnetic radiation a first a rotatable polarizer (WGP1) and a first rotatable element (RE1) can be referred to as a polarization state generator, while a combination of a second rotatable element (RE2) and a second rotatable polarizer (WGP2) and a detector (DET) of terahertz electromagnetic radiation considered as a polarization state detector. FIGS. 1D', 1D" and 1D''' show that a magnet can be placed with respect to a stage (STG) for use in practicing the Optical Hall Effect (OHE) methodology described elsewhere herein. FIGS. 1D' and 1D" suggest flipping the magnet and FIG. 1D''' shows two magnets on a support which can be positioned, (slid or rotated), to provide a North (N) or South (S) pole as desired or as an approach to modulation of signal during data acquisition. It is further noted that the Sample (S) could also be rotated during data acquisition to provide modulation. A chopper could be applied to provide a similar effect. As well, anywhere a magnet is applied it could be of a modulated strength, perhaps by being combined with an electromagnet.

Also shown in FIG. 1D is an optional Chamber (CHA) in which the Stage (STG) and Sample (S) can be present, and a temperature controller (HE) and Wires (W) to provide electric power thereto. In use these elements, (ie. (CHA) and (HE)), can be applied to control the atmospheric content and pressure adjacent to a Sample (S) surface, as well as the Temperature of the Sample (S). Atmospheric content can be controlled via Ports (PI) and, where required, (PO). Typically the atmosphere content will be controlled by flowing gas or liquid into Input Port (PI) and removing it via Output Port (PO). Controlling said atmospheric and temperature parameters while acquiring data can provide interesting insight to how, for instance, free charge carrier properties vary therewith via observation of changes in Mueller Matrix elements. See Knight et al. "In Situ Terahertz optical Hall Effect Measurement of Ambient Effects on Free Charge Carrier Properties of Epitaxial Graphene", Scientific Reports 7:5151, Jul. 11, 2017.

FIG. 1E shows another embodiment of a THz ellipsometer system developed by the J.A. Woollam Co. FIG. 1E' demonstrates that the stage in FIG. 1E can be rotated to effect an angle of incidence of a beam of electromagnetic radiation there-approaching FIG. 1E which shows a preferred embodiment of the present invention Terahertz Ellipsometer sequentially system comprising:
  a source (BWO) of terahertz electromagnetic radiation;
  a first rotatable polarizer (WGP1):
  a stage (STG) for supporting a sample (S);
  a second rotatable polarizer (WGP2);
  a detector (DET) of terahertz electromagnetic radiation.

Said terahertz ellipsometer or polarimeter system further comprises a first rotating element (REI) and second rotating element (RE2) between said source and detector of electromagnetic radiation.

In use said source of terahertz electromagnetic radiation directs a beam (BI) of terahertz frequency electromagnetic radiation of a fundamental frequency to pass through said first rotatable polarizer, then reflect from a sample (S) placed on said stage (STG) for supporting a sample, then pass through said second rotatable polarizer, and as output beam (BO) enter said detector of electromagnetic radiation as output beam (BO), wherein said beam also passes through said first rotating element (REI) and second rotating element (RE2).

Figure 3A:
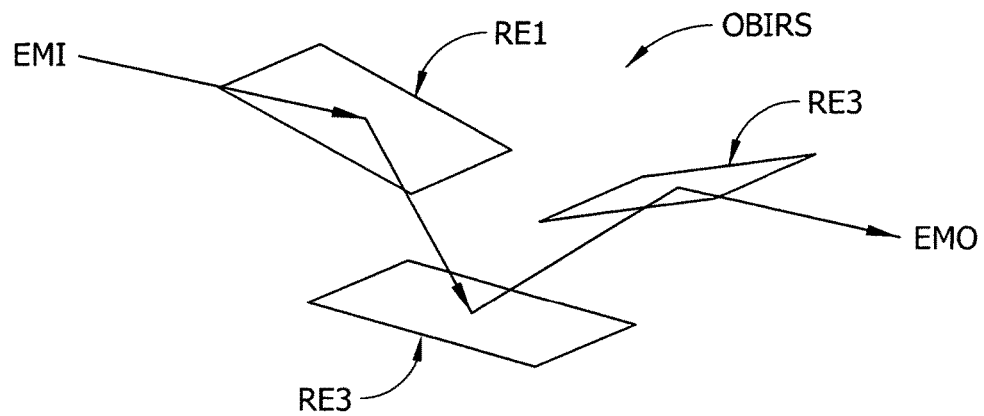
FIGS. 3A and 3B, there is represented in FIG. 3a, a three (3) bounce Odd Bounce image rotating system (OBIRS).
Figure 3B:
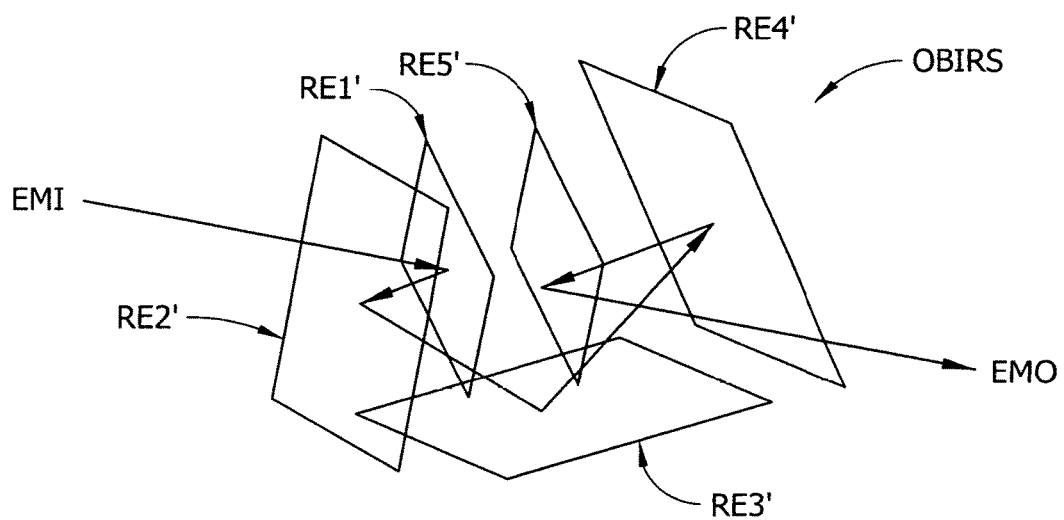
Figure 3C:
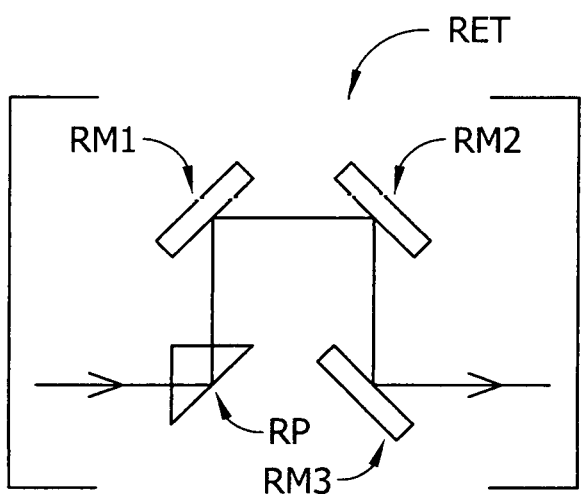
FIGS. 3C-3G show various designs for rotating compensator systems.
Figure 3D:
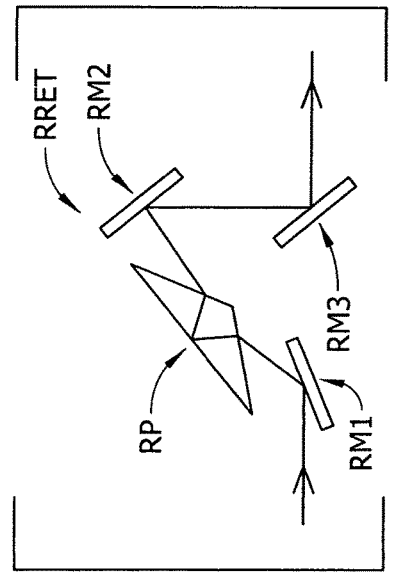
Figure 3E:
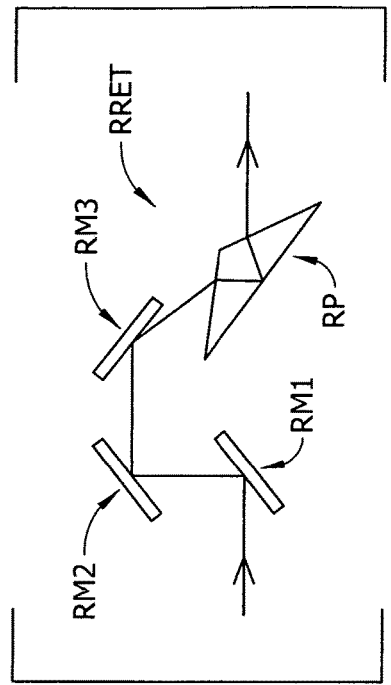
Figure 3F:
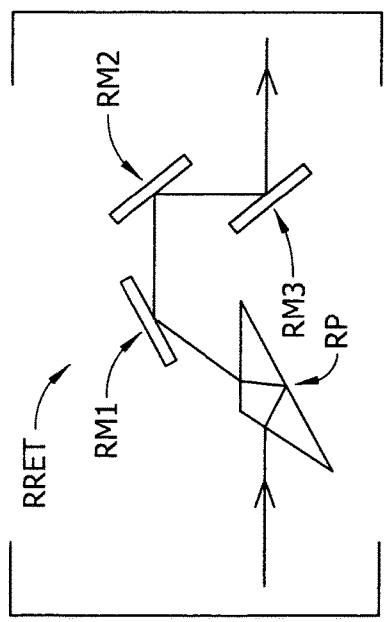
Figure 3G:
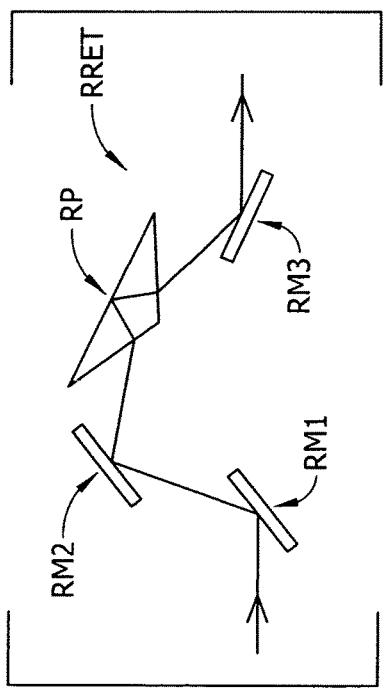

In more detail FIG. 1E shows a more detailed preferred presently disclosed terahertz ellipsometer sequentially system comprising:
  a backward wave oscillator (BWO);
  an optional frequency multiplier (FM);
  an optional first concave parabolic mirror (PM1),
  an optional reflecting means (Ml);
  a first rotatable wire grid polarizer (WGP1);
  an optional second concave parabolic mirror (PM2);
  a rotating wire grid polarizer (RWGP);
  a stage for (STG) supporting a sample (S);
  a rotating retarder (RRET) (comprising first, second, third and fourth elements as shown in FIGS. 3C-3G); said FIG. 3C demonstrating a preferred arrangement of:
    first (RP), second (RM1), third (RM2) and fourth (RM3) reflective elements from each of which, in use, an electromagnetic beam reflects once,
    said first reflective element (RP) being prism (RP) which receives a beam through a first side thereof and exits a reflected beam through a third side thereof,
    said reflection being from a second side thereof oriented at prism forming angles to said first and third sides; said elements (RP) (RM1) (RM2) (RM3) being oriented with respect to one another such that the locus of the beam reflecting from the second side of said prism approaches said second reflective side thereof at an angle equal to or greater than that required to achieve total internal reflection within said prism (RP),
    and such that the locus of beam reflected from the fourth element in the sequence of elements is substantially co-linear and without deviation or displacement from the locus of the beam received by the first element in said sequence of elements,
an optional third concave parabolic mirror (PM3);
a second rotatable wire grid polarizer (WGP2);
an optional fourth concave parabolic mirror (PM4); and
a Golay cell detector (DET).

Assuming optional elements are present, in use said backward wave oscillator (BWD) directs a beam of terahertz frequency electromagnetic radiation of a fundamental frequency to said frequency multiplier (FM), from which frequency multiplier (FM) a beam comprising a desired frequency is caused to be reflected from said first concave parabolic mirror (PMI) as a substantially collimated beam, said substantially collimated beam then being directed to reflect from said reflecting means (MI) and pass through said first rotatable wire grid polarizer (WGP1) and reflect from said second concave parabolic mirror (PM2) through said rotating wire grid polarizer (RWGP), then reflect from a sample (S) placed on said stage (STG) for supporting a sample, then pass through said rotating retarder (RRET), reflect from said third parabolic mirror (PM3), pass through said second rotatable wire grid polarizer (WGP2), then reflect from said fourth concave parabolic mirror (PM4) and enter said Golay cell detector (DET).

FIG. 1E' shows that that the FIGS. 1D and 1E terahertz ellipsometer system can further comprise means for rotating, as a unit, said:
stage (STG) for supporting a sample (S);
rotating retarder comprising first (RP), second (RM1), third (RM2) and fourth (RM3) elements;
third concave parabolic mirror (PM3);
second rotatable wire grid polarizer (WGP2);
fourth concave parabolic mirror (PM4); and
Golay cell detector (DET);
about a vertical axis centered at a midpoint of said stage (STG) for supporting a sample (S) such that the angle of incidence (6) at which said beam of terahertz frequency electromagnetic radiation approaching from said rotating wire grid polarizer (RWGP), and the angle of reflection (e) of said beam from said sample (S) placed on said stage (STG) for supporting a sample, can be adjusted.

FIG. 1E is to also be interpreted to, in addition, or as an option, enable said terahertz ellipsometer system to further comprise means for rotating, as a unit, said:
backward wave oscillator (BWO);
frequency multiplier (FM) if present;
first concave parabolic mirror (PMI) if present;
reflecting means (MI) if present;
rotatable wire grid polarizer (WGPI);
second concave parabolic mirror (PM) if present;
rotating wire grid polarizer (RWGP);
about a vertical axis centered at a midpoint of said stage (STG) for supporting a sample (S) such that the angle of incidence (9) at which said beam of terahertz frequency electromagnetic radiation approaching from said rotating wire grid polarizer (RWGP), and the angle of reflection (e) of said beam from said sample (S) placed on said stage (STG) for supporting a sample, can be adjusted. In practice either the components on the Source (BWO) and/or Detector (DET) side of the stage (STG), along with the stage can be rotated to set an Angle-of-Incidence of a Terahertz beam onto a sample.

The terahertz ellipsometer system can further comprise a beam chopper (CHP), said beam chopper (CHP) being of any functional design, but typically being a rotating wheel with a plurality of openings therein through which the terahertz electromagnetic radiation beam can pass, said chopper being placed the locus of the terahertz electromagnetic radiation beam at some point between said backward wave oscillator and said Golay cell detector, said wheel being made from high density polyethelyene. Note the position of the chopper (CH) in FIG. 1E is demonstrative, not limiting. The chopper (CHP) can be located at any functional location in the terahertz ellipsometer system.

It is noted that said terahertz ellipsometer system is typically oriented to mount samples (B) to said stage (8TG) for supporting a sample so that said sample (S) is in a vertical plane as observed in laboratory coordinates. FIG. 1E' shows a system that allows said terahertz ellipsometer system to orient the stage (STG) for supporting a sample (8) in a horizontal plane. Note that the stage (STG) for supporting a sample (S) is oriented to support a sample in a horizontal plane and in which the beam is directed thereto via left and right vertical sequences, each of first (FLS/FRS) second (BLB/BRB) and third (TLS/TRS) elements, such that the terahertz frequency electromagnetic beam exiting said rotating wire grid polarizer (RWGP) reflects from the first" left side element (FLS) to the second left side "element (BLS), then to the third right side element (TRS), from which it is directed to reflect from a sample (S) placed on the stage (STG) in a horizontal plane toward the third left side element (TLS), which reflects said beam to the second right: side element (BRS) toward said first right side element (FRB), from which said beam is directed into said rotating retarder (RRET), (see FIG. 1E).

Figure 1F:
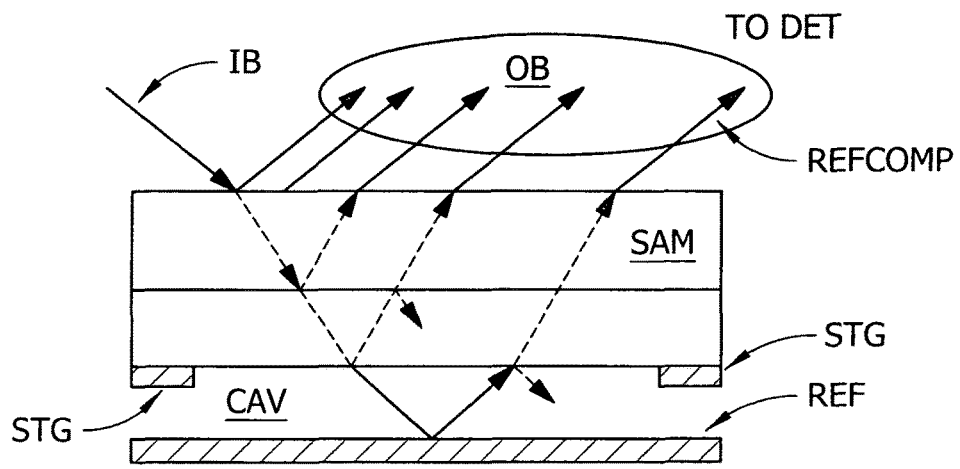
FIG. 1F shows better detail of a sample adjacent to a reflective Cavity.

FIG. 1F shows demonstrative detail of a Sample (S) on a Stage (STG), (shown as "split" to avoid it's affecting a beam which passes through a Sample (SAM)), adjacent to a Cavity (CAV) having a reflective surface (REF). With reference to FIG. 2B it can be appreciated that an effective Cavity (CAV) can be formed between a magnetic casing plate (MCP) and Interface Plate (IP), and a Motor (SP) applied to control the geometry of the Cavity (CAV). Note that the effect of the Cavity (CAV) and reflective surface (REF) thereof, causes an enhanced coherent signal to exit the Sample (S) and proceed toward the Detector (DET) of an ellipsometer system utilized. It is also noted that representative materials from which to construct reflective surfaces (REF) include metals, highly doped semiconductors ($10^{18}$ $cm^{-3}$), Bragg Dielectric reflectors, total internal reflection condition systems, and long cavity tunnel reflectors.

Figure 1G:
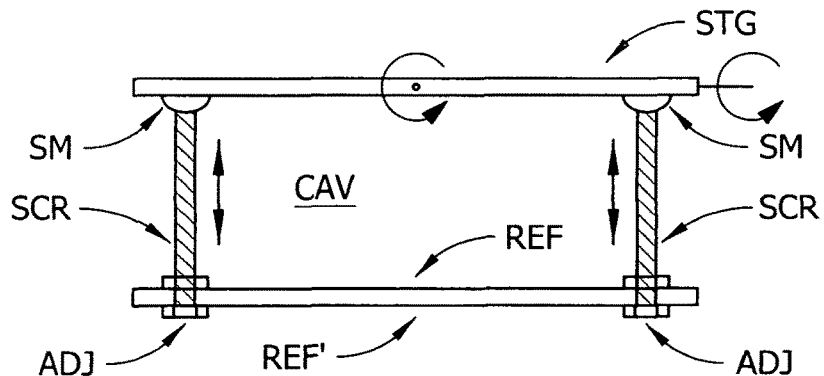
FIGS. 1G and 1H demonstrate a non-limiting stage that allows tip/tilt to be accomplished for the purpose of adjusting a cavity geometry, and for adjusting angle and plane of incidence of an ellipsometer beam with respect to a sample surface.
Figure 1H:
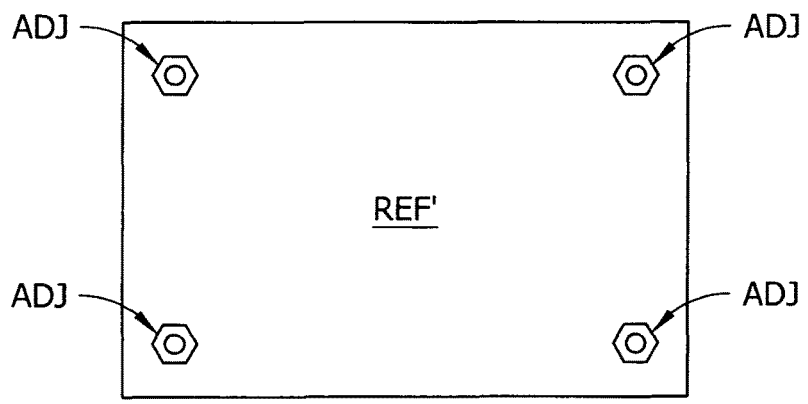

FIGS. 1G and 1H are included for general insight and are not limiting. FIG. 1G indicates that a Cavity (CAV) is formed between the lower surface of a Stage (STG) for supporting s Sample, (as generally shown in, for instance, FIG. 1D), and a Reflector (REF) upper surface. One way to enable adjusting the relative orientations of said Stage (STG) and Reflector (REF) is to place Screws (SCR) at each corner of the Reflector (R) which are secured so that rotation thereof causes the Screws to extend or retract with respect to said Reflector (RFE). The Screws (SCR) are affixed to the Stage (STG) via Securing Means (SM) that allow Screw rotation therewithin, while maintaining a fixed position of the end thereof with respect to said Stage (STG). It should be apparent the Stage (STG) can be effectively rotated in Tip and Tilt directions by selective rotation (note the arrows showing Stage (STG) Tip and Tilt) of the Screws until a desired Cavity Geometry is achieved. With a Cavity (CAV) geometry achieved as demonstrated, a further Stage (STG) Tip/Tilt can be achieved as suggested by FIG. 1E'. Again, FIGS. 1F-1H are not limiting. They simply serve to give insight to the need to be able to adjust a Stage (STG) for two purposes. One is to provide a desired Cavity (CAV) geometry and the other is the to enable adjustment of the Angle-of-Incidence an ellipsometer beam makes with respect to a Sample (SAM) surface.

Figure 2A:
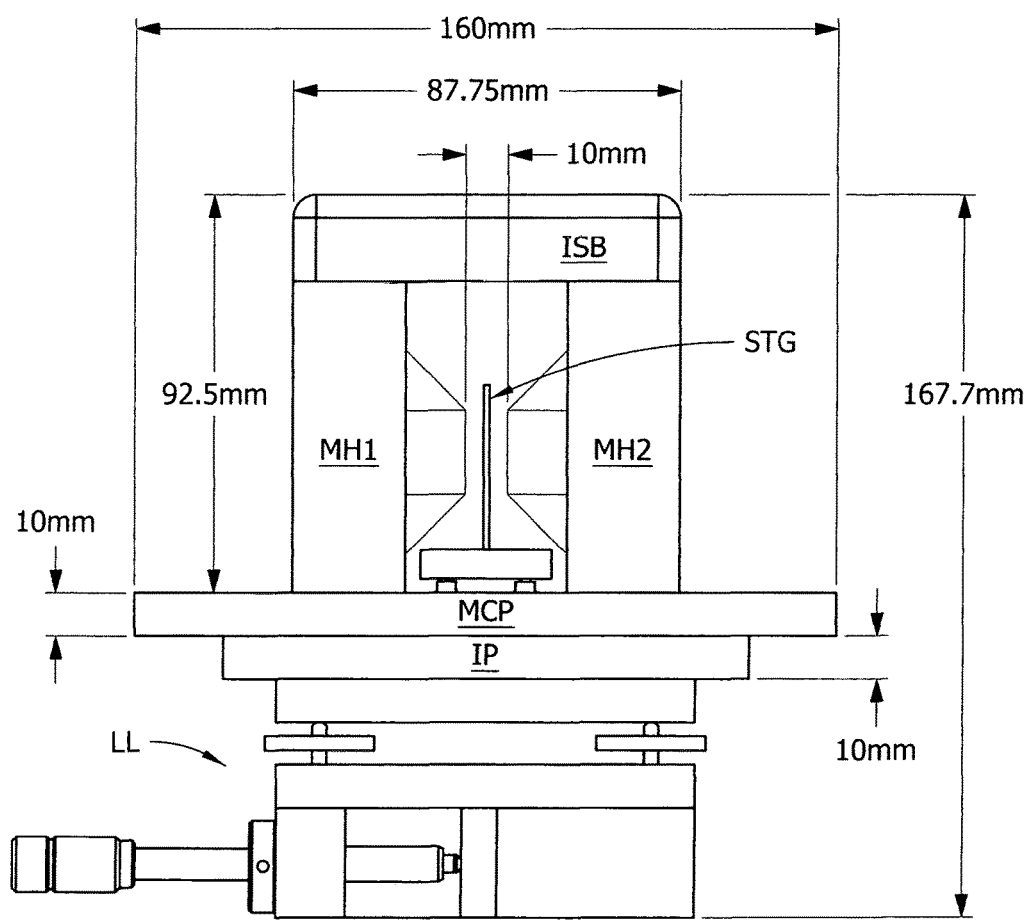
FIGS. 2A-2E there is shown a stage for supporting a sample that is suitable for use in the preferred embodiment of the present invention.
Figure 2C:
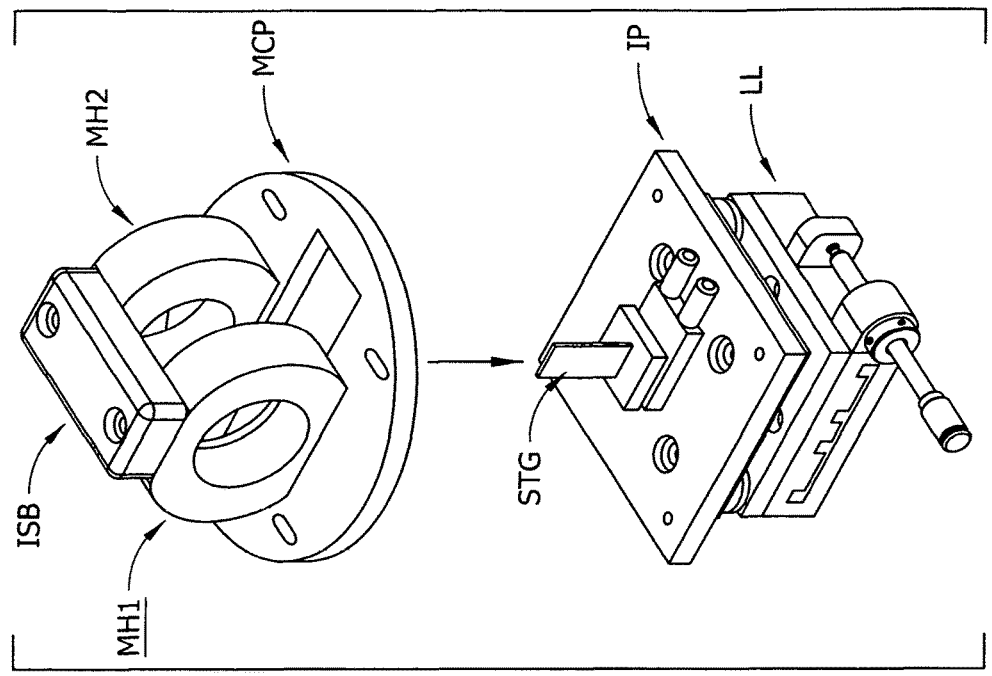
Figure 2B:
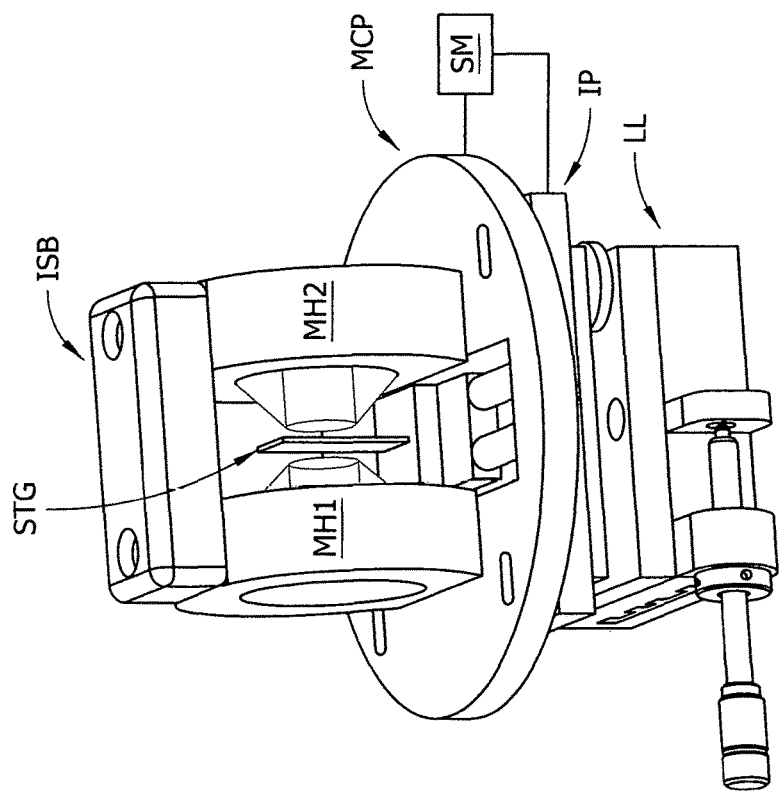
Figure 2E:
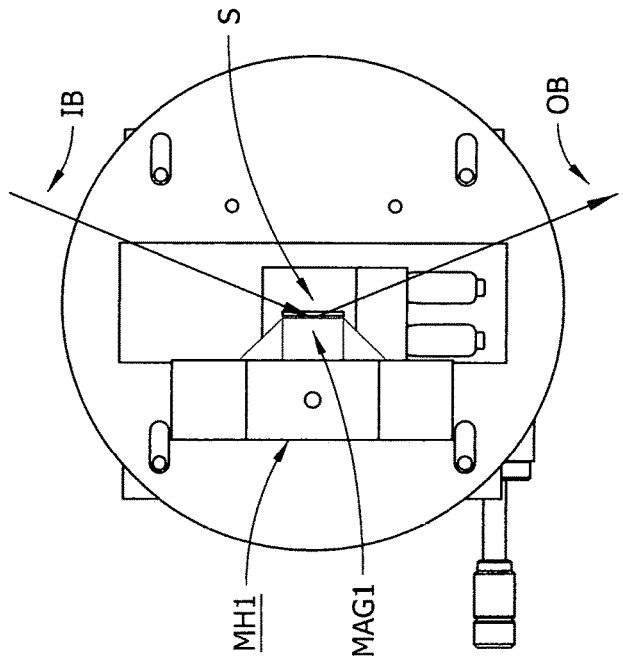
Figure 2D:
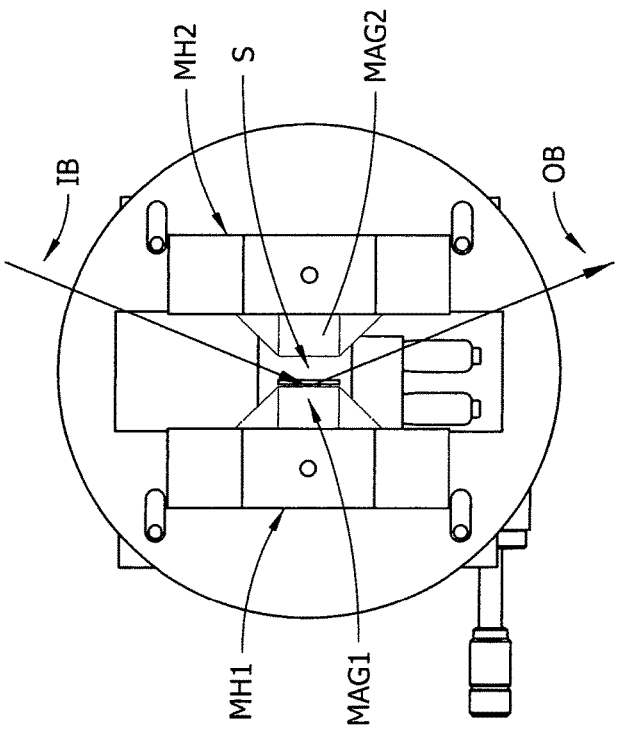

Turning now to FIGS. 2A-2E there is shown a stage system for supporting (STG) a sample (S) that is suitable for use in the present invention, (Note FIG. 2A provides exemplary, not limiting dimensions of a preferred stage). Said stage system can be described as being comprised of:
 a) a mechanism for adjusting tip and/or tilt of a surface of a sample (S) placed on a surface of said stage (STG) for supporting a sample (S);
 b) an interface plate (IP) comprising said stage for supporting a sample, and which is controlled by said mechanism for adjusting the tip and/or tilt of a surface of a sample (S) placed thereon on a surface of said stage;
 c) a magnetic casing plate (MCP) comprising at least one magnet holder (MH1) (MH2) for securing at least one magnet thereto, said magnetic casing plate (MCP) and interface plate (IP) being off-settable from one another and controlled in relative orientation with respect to one another by, for instance, a motor, and wherein a selection form the group consisting of: one magnet holder (MH1); and two magnet holders (MH1) (MH2), which can be, but do not necessarily need to be so, interconnected by a magnetic material. (eg. Iron), support bar (ISB) as shown in FIG. 2C, and in which the sample supporting stage (STG) can be adjusted to be at a desired distance from and in a desired orientation with respect to said magnet(s) (MAG1) (MAG2) in said holder(s) thereof (MH1) (MH2) by said mechanism for adjusting tip and/or tilt of a surface of a sample (S) placed on a surface of said stage (STG) for supporting a sample (S).

The sample (S) supporting stage (STG) can be adjusted to be at a desired distance from a contained magnet (MAGI) (MAG2), by placing at least one layer of spacer material, (eg. Tape), between the backside of said sample (S) and said sample supporting stage (STG), and/or by application of a motor, (typically a Stepper Motor (SM) or the like), that controls, for instance, relative orientation of the magnetic casing plate (MCP) and interface plate (IP) with respect to one another.

It is convenient to use FIG. 1D to describe the various types of ellipsometers which can be configured from the shown components. For instance, a Rotating Polarizer (RP) ellipsometer can be configured by causing Polarizer Element (WGP1) to rotate during data acquisition. A Rotating Analyzer (RA) ellipsometer is configured by causing said Element (WGP2) to rotate during data acquisition. A Rotating Compensator ellipsometer is configured by making either of the First (RE1) or Second (RE2) shown Rotating Elements be a Compensator and causing it to rotate during data acquisition. If both (RE1) and (RE2) are made to be compensators and both are caused to rotate during data acquisition, the ellipsometer is a Dual Rotating Compensator system. (eg. J.A. Woollam Co. RC2®). This is mentioned as the Cavity (CAV) enhancement of an Output Signal (OB) can be used in any ellipsometer configuration, even when the system is not applied to investigating the Optical Hall Effect. There are also Modulation element (ME) ellipsometers, in which an element is made to change some parameter value rather than as caused by rotation of an element. The present invention can be configured as a modulation element system by causing the Cavity (CAV) geometry to be changed, (ie. modulated), while data is being acquired. This is mentioned as the Cavity (CAV) geometry can be varied very rapidly, thereby leading to a "fast" data acquisition ellipsometer. Again, it is not necessary that the modulation element system alluded to be applied only in practicing Optical Hall Effect investigation. In addition, it is possible to augment the preferred permanent magnet with an electromagnet and alter the "B" filed applied to a sample by varying current therethrough. An electromagnet can be used exclusively, but this is known in the art.

Turning now to FIGS. 3A and 3B, there is represented in FIG. 3A, a three (3) bounce Odd Bounce image rotating system (OBIRS) comprising three (3) reflective elements (REI), (RE2) and (RE3), oriented with respect to one another such that an input beam of electromagnetic radiation (EMI) exits as an output beam of electromagnetic radiation (EMO) without any deviation or displacement being entered into the locus thereof. FIG. 3B demonstrates a five (5) bounce odd bounce image rotating system (OBIRS) wherein five reflective elements (REI'), (RE2') (RE3'), (RE4') and (RE5') oriented with respect to one another such an input beam-of electromagnetic radiation (EMI) exits as an output beam of electromagnetic radiation (EMO) without any deviation or displacement being entered into the locus thereof. Note generally that the angle of incidence of the (EMI) and (EMO) beams of electromagnetic radiation are nearer normal than is the case in the FIG. 3A three (3) bounce odd bounce image rotating system (OBIRS). This is beneficial in that the closer to normal the angle of incidence, the less aberration effects are entered to the beam. However, it is also to be appreciated that construction of the FIG. 3B system is more difficult than is construction of a FIG. 3S system.

FIGS. 3C-3G show various designs for rotating compensator systems, identifying Reflectors (RM1) (RM2) (RM3) (RM4), and a Total Internal Reflection Prism (RP) reflecting surface.

Figure 4B:
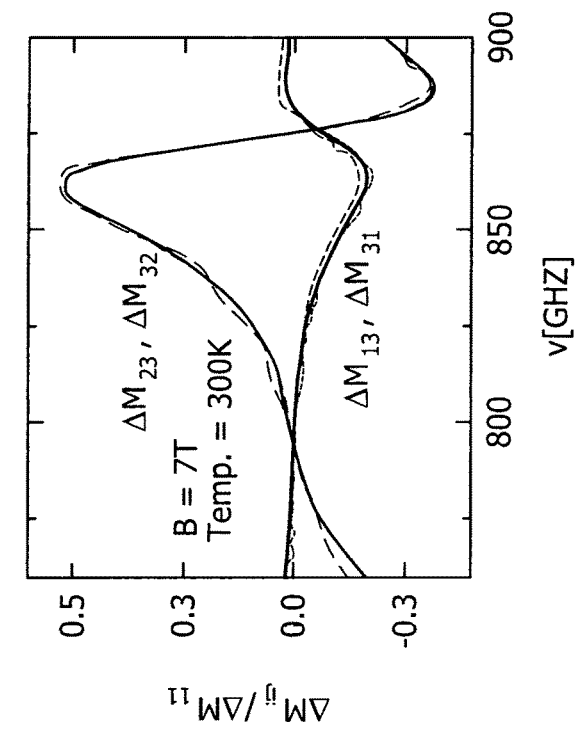
FIGS. 4A and 4B show Mueller Matrix data obtained using the present invention which comprises the stage of FIGS. 2a-2e that incorporates a permanent magnet and which is applied at room temperature.
Figure 4A:
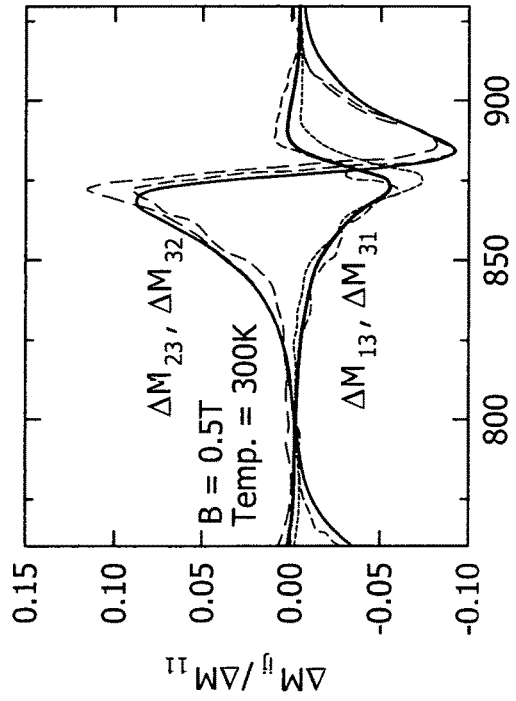
Figure 4E:
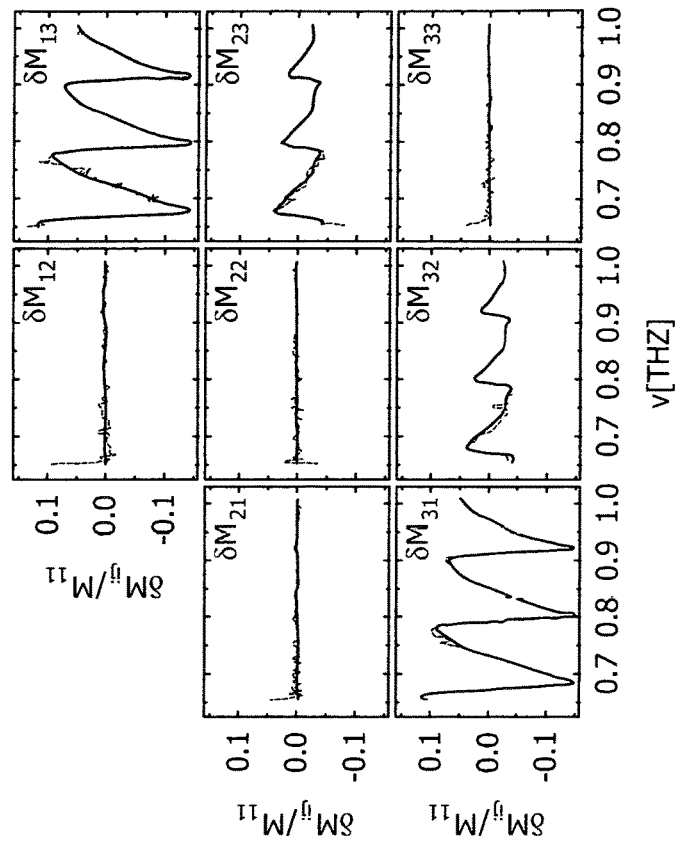
FIG. 4E shows Mueller Matrix Elements M13/M11, M31/M11, M23/M11 and M32/M11 obtained with a B field applied, and wherein the data shown is the difference between that obtained when the Magnet is placed with the North Pole facing one direction and then the other.
Figure 4D:
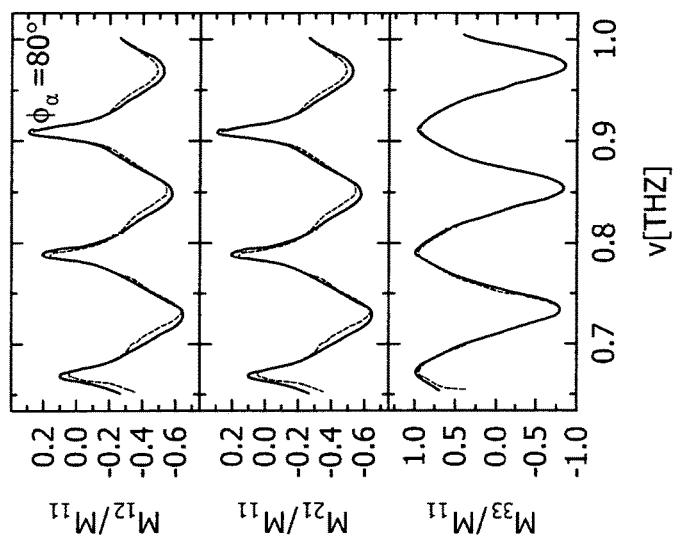
FIG. 4D shows M12/M11, M21/M11 and M33/M11 Mueller Matrix components obtained with no B Field applied.

FIGS. 4A and 4B show Mueller Matrix data obtained using the present invention which comprises the stage of FIGS. 2A-2E that incorporates a permanent magnet and which is applied at room temperature, and data obtained from a system which is applied in at much higher B fields, again at room temperature, respectively. To be noted is that the plots are generally similar, with the difference being that the FIG. 4B data is a better match to a sample model. This shows that the present invention, which uses much less costly and more easily accessible equipment, can be used to provide reasonably good data. FIG. 4C shows a general Mueller Matrix configuration, and FIG. 4D shows M12/M11, M21/M11 and M33/M11 Mueller Matrix components obtained with no B Field applied. FIG. 4E shows Mueller Matrix Elements M13/M11, M31/M11, M23/M11 and M32/M11 obtained by applying the present invention method with a B field applied, and wherein the data shown is the difference ($\sigma$) between that obtained when the Magnet is placed with the North Pole facing one direction and then the other.

Figure 5:
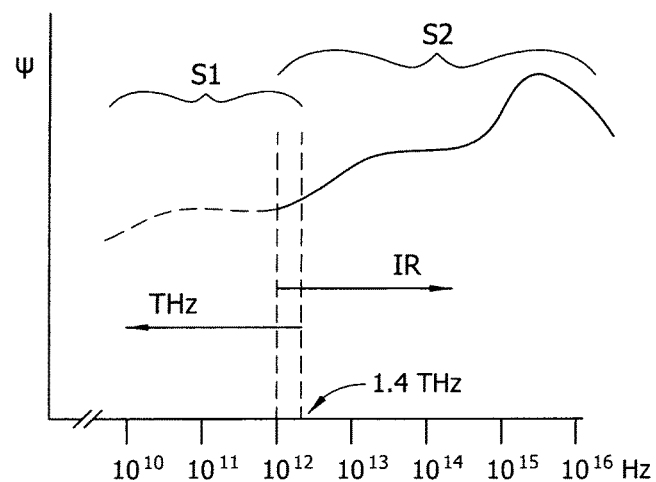
FIG. 5 is included to indicate that it is optimum to provide VIS-MIR and FIR-THz sources that provide output which overlaps in the range of about 1.0 to 1.4 THz.

FIG. 5 is included to indicate that it is optimum to provide VIS-MIR and FIR-THz sources that provide output which overlaps in the range of about 1.0 to 1.4 THz. FIG. 5 shows that a preferred embodiment of the system allows sample investigation in both the THz and IR ranges, (eg. from 300 GHz to about 1.4 THz, and from about 1.0 THz and higher frequency). Further, it is indicated that below about 1.4 THz a first (31) is used to provide the electromagnetic radiation, and above about 1.0 THz a second (S2) Source is used to provide the electromagnetic radiation. FIG. 5 shows an overlap in the range of about 1.0 to about 1.4 THz, and that a described system preferably provides the same results, (eg.

ellipsometic PSI and/or DELTA), when Detector output is analyzed- to provide, for instance, a Sample characterizing PSI or DELTA. FIG. 5 should be viewed as demonstrating a concrete and tangible presentation of results which can be achieved by application of a described Invention.

Figure 6:
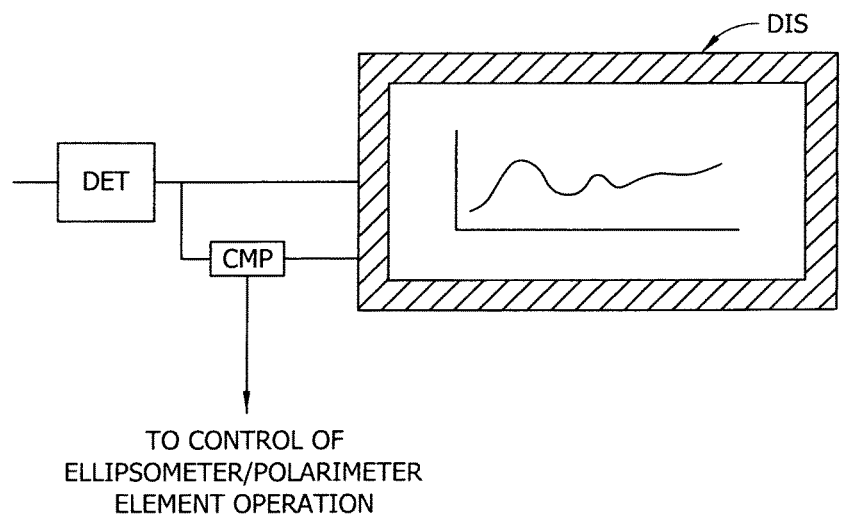
FIG. 6 demonstrates displaying data (DIS) provided by a Detector (DET).

FIG. 6 demonstrates displaying data (DIS) provided by a Detector (DET), (DET in FIGS. 1d and 1e), obtained by practice of described systems using machine readable media of a computer (CMP), as well as indicates the Computer (CMP) can control Ellipsometer/Polarimeter elements operation.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in scope only by the Claims.

We claim:

1. A method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:
   a) providing an ellipsometer comprising:
      a source of a beam of electromagnetic radiation characterized by at least one wavelength in a selection from the group consisting of the:
         Vacuum Ultraviolet;
         Near-Ultraviolet;
         Mid-Ultraviolet;
         Visible;
         NIR;
         MIR;
         FIR; and
         THz ranges;
      a polarizer;
   a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s), said stage being present inside a chamber that comprises at least one selection from the group consisting of:
      at least an input port for use in controlling the atmospheric content and pressure inside said chamber; and
      a temperature controller inside said chamber
      an analyzer; and
      a detector of relevant electromagnetic radiation wavelengths; and
      further providing a source of a magnetic field;
   b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;
   c) setting at least one of the temperature and/or atmospheric content and pressure thereof inside said chamber;
   d) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;
   e) from data accumulated by said detector with the system adjusted as described in steps b) and c), evaluating anisotropic values for at least a partial Jones or Mueller Matrix; and
   f) from said anisotropic values for said at least a partial Jones or Mueller Matrix determining at least one of the free charge carrier longitudinal and/or transversal effective masses, and/or concentration, and/or mobility and/or type;
   said method being characterized in that it comprises at least one selection from the group consisting of:
   a1') data is accumulated with the source provided beam of electromagnetic radiation set so that it provides at least one substantially exact multiple of an optical path length within said sample;
   a2') nine Mueller Matrix are evaluated, said nine elements being M11, M12, M13, M21, M22, M23, M31, M32 and M33, and wherein each Mueller Matrix elements M12, M13, M21, M22, M23, M31, M32 and M33 is divided by the value of M11 prior to use in evaluating free charge carrier longitudinal and transversal effective masses, concentration, mobility and type;
   a3') at least a partial Mueller matrix is determined and, of the Mueller Matrix elements M11, M12, M13, M21, M22, M23, M31, M32 and M33 that can be determined, at least M11, and at least one of M23 and M32 are, said approach to determining values for M11, and at least one of M23 and M32 being distinguished in that data is determined by a selection from the group consisting of:
      placing said sample on said stage for supporting a sample with the back side thereof in contact with said stage and obtaining a first set of data, then flipping said sample so that it's surface is in contact with said stage and obtaining a second set of data; and
      first placing the north pole of a permanent magnet near to the sample and obtaining a first set of data, and then placing the south pole of the same or another magnet so that the south pole thereof is near the sample and obtaining a second set of data,
   followed by subtracting said second set of data from said first, or vice-versa, for each of the resulting M11, and at least one of said resulting M23 and M32 Mueller Matrix elements determined, and wherein each determined M23 and M32 is divided by M11, prior to using said resulting at least one of M23 and M32 values as data upon which to regress a model of said sample that includes free charge carrier longitudinal and transversal effective masses, concentration, mobility and type, thereby allowing their evaluation;
   a4') at least one of M13 and M3 is determined in addition to M11 by the procedure of obtaining a first set of data with the sample back side in contact with said stage and then flipping said sample or over so that it's surface is in contact with said stage and obtaining a second set of data; or by first placing the north pole of a permanent magnet near to the sample and obtaining a first set of data, and then placing the south pole of the same or another magnet so that the it is near the sample and obtaining a second set of data;
   and then subtracting said second set of data from said first, or vice-versa, for each of the resulting M11, and at least one of said resulting M13 and M31 Mueller Matrix elements determined, prior to using said resulting at least one of M23 and M32 and at least one of M13 and M31 values as data upon which to simultaneously regress a model of said sample that includes free charge carrier longitudinal and transversal effective masses, concentration, mobility and type, thereby allowing their evaluation;

a5') at least a partial Mueller matrix is determined and, of the Mueller Matrix elements M11, M12, M13, M21, M22, M23, M31, M32 and M33 that can be determined, at least M11, and at least one of M13 and M31 are, said approach to determining values for M11, and at least one of M13 and M31 being distinguished in that data is determined by a selection from the group consisting of:

placing said sample on said stage for supporting a sample with the back side thereof in contact with said stage and obtaining a first set of data, then flipping said sample so that it's surface is in contact with said stage and obtaining a second set of data; and by first placing the north pole of a permanent magnet near to the sample and obtaining a first set of data, and then placing the south pole of the same or another permanent magnet so that is near the sample and obtaining a second set of data;

and then subtracting said second set of data from said first, or vice-versa, for each of the resulting M11, and at least one of said resulting M23 and M32 Mueller Matrix elements determined, and wherein each determined M13 and M31 is divided by M11, prior to using said resulting at least one of M13 and M31 values as data upon which to regress a model of said sample that includes free charge carrier longitudinal and transversal effective masses, concentration, mobility and type, thereby allowing their evaluation;

a6') at least one of M32 and M23 is determined in addition to M11 by the procedure of data being determined by obtaining a first set of data with the sample back side in contact with said stage and then flipping said sample over so that it's surface is in contact with said stage and obtaining a second set of data; or by first placing the north pole of a permanent magnet near to the sample and obtaining a first set of data, and then placing the south pole of the same or another permanent magnet so that is near the sample and obtaining a second set of data, and then subtracting said second set of data from said first for each of the resulting M11, and at least one of said resulting M23 and M32 Mueller Matrix elements determined, prior to using said resulting at least one of the M23 and M32 and at least one of M23 and M32 values as data upon which to simultaneously regress a model of said sample that includes free charge carrier longitudinal and transversal effective masses, concentration, mobility and type, thereby allowing their evaluation;

a7') Mueller Matrix element M11, and at least one selection from the group of elements consisting of M12, M13, M23, or at least one selection from the group of elements consisting of M12, M13, M33 is evaluated by, for each selection, a selection from the group consisting of:

first placing said sample on said stage for supporting a sample with the back side thereof in contact with said stage and obtaining a first set of data, and second flipping said sample so that it's surface is in contact with said stage and obtaining a second set of data; and by first placing the north pole of a permanent magnet near to the sample and obtaining a first set of data, and second placing the south pole of the same or another magnet so that it is near the sample and obtaining a second set of data;

followed by subtracting the first from the second or the second from the first obtained set of data for each selection from the group of elements consisting of at least one selection from the group consisting of M12, M13, M23, or at least one selection from the group of elements consisting of M12, M13, M33;

followed by dividing said result(s) by M11, before, from said anisotropic value(s), determining at least one of the free charge carrier concentration and/or mobility.

2. A method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:

a) providing an ellipsometer comprising:

a source of a beam of electromagnetic radiation characterized by at least one wavelength in a selection from the group consisting of the:

Vacuum Ultraviolet;

Near-Ultraviolet;

Mid-Ultraviolet;

Visible;

NIR;

MIR;

FIR; and

THz ranges;

a polarizer;

a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s);

an analyzer; and a detector of relevant electromagnetic radiation wavelengths; and further providing a source of a magnetic field;

b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;

c) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;

d) from data accumulated by said detector with the system adjusted as described in steps b) and c), evaluating anisotropic values for at least a partial Jones or Mueller Matrix; and e) from said anisotropic values for said at least a partial Jones or Mueller Matrix determining at least one of the free charge carrier longitudinal and/or transversal effective masses, and/or concentration, and/or mobility and/or type;

said method being characterized in that:

data is accumulated with the source provided beam of electromagnetic radiation set so that it provides at least one substantially exact multiple of an optical path length within said sample.

3. A method as in claim 2 in which the stage is present inside a chamber that comprises at least one selection from the group consisting of:
- at least an input port for use in controlling the atmospheric content and pressure inside said chamber; and
- a temperature controller inside said chamber;

and in which the method further comprises controlling at least one of:
- atmospheric content and/or pressure and/or temperature inside said chamber, while practicing step c).

4. A method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:

a) providing an ellipsometer comprising:
 a source of a beam of electromagnetic radiation characterized by at least one wavelength in a selection from the group consisting of the:
 Vacuum Ultraviolet;
 Near-Ultraviolet;
 Mid-Ultraviolet;
 Visible;
 NIR;
 MIR;
 FIR; and
 THz ranges;
 a polarizer;
 a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s);
 an analyzer; and
 a detector of relevant electromagnetic radiation wavelengths; and
 further providing a source of a magnetic field;

b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;

c) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;

d) from data accumulated by said detector with the system adjusted as described in steps b) and c), evaluating anisotropic values for at least a partial Jones or Mueller Matrix; and e) from said anisotropic values for said at least a partial Jones or Mueller Matrix determining at least one of the free charge carrier longitudinal and/or transversal effective masses, and/or concentration, and/or mobility and/or type;

said method being characterized in that:

nine Mueller Matrix are evaluated, said nine elements being M11, M12, M13, M21, M22, M23, M31, M32 and M33, and wherein each Mueller Matrix elements M12, M13, M21, M22, M23, M31, M32 and M33 is divided by the value of M11 prior to use in evaluating free charge carrier longitudinal and transversal effective masses, concentration, mobility and type.

5. A method as in claim 4 in which the stage is present inside a chamber that comprises at least one selection from the group consisting of:
- at least an input port for use in controlling the atmospheric content and pressure inside said chamber; and
- a system for controlling temperature controlling inside said chamber;

and in which the method further comprises controlling at least one of:
- atmospheric content and/or pressure and/or temperature inside said chamber, while practicing step c).

6. A method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:

a) providing an ellipsometer comprising:
 a source of a beam of electromagnetic radiation characterized by at least one wavelength in a selection from the group consisting of the:
 Vacuum Ultraviolet;
 Near-Ultraviolet;
 Mid-Ultraviolet;
 Visible;
 NIR;
 MIR;
 FIR; and
 THz ranges;
 a polarizer;
 a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s);
 an analyzer; and
 a detector of relevant electromagnetic radiation wavelengths; and
 further providing a source of a magnetic field;

b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;

c) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;

d) from data accumulated by said detector with the system adjusted as described in steps b) and c), evaluating anisotropic values for at least a partial Jones or Mueller Matrix; and e) from said anisotropic values for said at least a partial Jones or Mueller Matrix determining at least one of the free charge carrier longitudinal and/or transversal effective masses, and/or concentration, and/or mobility and/or type;

said method being characterized in that:
at least a partial Mueller matrix is determined and, of the Mueller Matrix elements M11, M12, M13, M21, M22, M23, M31, M32 and M33 that can be determined, at least M11, and at least one of M23 and M32 are, said approach to determining values for M11, and at least one of M23 and M32 being distinguished in that data is determined by a selection from the group consisting of:

placing said sample on said stage for supporting a sample with the back side thereof in contact with said stage and obtaining a first set of data, then flipping said sample so that it's surface is in contact with said stage and obtaining a second set of data; and first placing the north pole of a permanent magnet near to the sample and obtaining a first set of data, and then placing the south pole of the same or another magnet so that the south pole thereof is near the sample and obtaining a second set of data, followed by subtracting said second set of data from said first, or vice-versa, for each of the resulting M11, and at least one of said resulting M23 and M32 Mueller Matrix elements determined, and wherein each determined M23 and M32 is divided by M11, prior to using said resulting at least one of M23 and M32 values as data upon which to regress a model of said sample that includes free charge carrier longitudinal and transversal effective masses, concentration, mobility and type, thereby allowing their evaluation.

7. A method as in claim 6 in which the stage is present inside a chamber that comprises at least one selection from the group consisting of:

at least an input port for use in controlling the atmospheric content and pressure inside said chamber; and a temperature controller inside said chamber;

and in which the method further comprises controlling at least one of:

atmospheric content and/or pressure and/or temperature inside said chamber, while practicing step c).

8. A method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:

a) providing an ellipsometer comprising:
a source of a beam of electromagnetic radiation characterized by at least one wavelength in a selection from the group consisting of the:
Vacuum Ultraviolet;
Near-Ultraviolet;
Mid-Ultraviolet;
Visible;
NIR;
MIR;
FIR; and
THz ranges;
a polarizer;
a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s);
an analyzer; and
a detector of relevant electromagnetic radiation wavelengths; and
further providing a source of a magnetic field;

b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;

c) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;

d) from data accumulated by said detector with the system adjusted as described in steps b) and c), evaluating anisotropic values for at least a partial Jones or Mueller Matrix; and e) from said anisotropic values for said at least a partial Jones or Mueller Matrix determining at least one of the free charge carrier longitudinal and/or transversal effective masses, and/or concentration, and/or mobility and/or type;

said method being characterized in that:
at least one of M13 and M3 is determined in addition to M11 by the procedure of obtaining a first set of data with the sample back side in contact with said stage and then flipping said sample or over so that it's surface is in contact with said stage and obtaining a second set of data; or by first placing the north pole of a permanent magnet near to the sample and obtaining a first set of data, and then placing the south pole of the same or another magnet so that the it is near the sample and obtaining a second set of data;

and then subtracting said second set of data from said first, or vice-versa, for each of the resulting M11, and at least one of said resulting M13 and M31 Mueller Matrix elements determined, prior to using said resulting at least one of M23 and M32 and at least one of M13 and M31 values as data upon which to simultaneously regress a model of said sample that includes free charge carrier longitudinal and transversal effective masses, concentration, mobility and type, thereby allowing their evaluation.

9. A method as in claim 8 in which the stage is present inside a chamber that comprises at least one selection from the group consisting of:
   at least an input port for use in controlling the atmospheric content and pressure inside said chamber; and
   a temperature controller inside said chamber;
and in which the method further comprises controlling at least one of:
   atmospheric content and/or pressure and/or temperature inside said chamber, while practicing step c).

10. A method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:
   a) providing an ellipsometer comprising:
      a source of a beam of electromagnetic radiation characterized by at least one wavelength in a selection from the group consisting of the: Vacuum Ultraviolet;
         Near-Ultraviolet;
         Mid-Ultraviolet;
         Visible;
         NIR;
         MIR;
         FIR; and
         THz ranges;
      a polarizer;
      a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s);
      an analyzer; and
      a detector of relevant electromagnetic radiation wavelengths; and
   further providing a source of a magnetic field;
   b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;
   c) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;
   d) from data accumulated by said detector with the system adjusted as described in steps b) and c), evaluating anisotropic values for at least a partial Jones or Mueller Matrix; and
   e) from said anisotropic values for said at least a partial Jones or Mueller Matrix determining at least one of the free charge carrier longitudinal and/or transversal effective masses, and/or concentration, and/or mobility and/or type;

said method being characterized in that:
at least a partial Mueller matrix is determined and, of the Mueller Matrix elements M11, M12, M13, M21, M22, M23, M31, M32 and M33 that can be determined, at least M11, and at least one of M13 and M31 are, said approach to determining values for M11, and at least one of M13 and M31 being distinguished in that data is determined by a selection from the group consisting of:
   placing said sample on said stage for supporting a sample with the back side thereof in contact with said stage and obtaining a first set of data, then flipping said sample so that it's surface is in contact with said stage and obtaining a second set of data; and
   by first placing the north pole of a permanent magnet near to the sample and obtaining a first set of data, and then placing the south pole of the same or another permanent magnet so that is near the sample and obtaining a second set of data;
   and then subtracting said second set of data from said first, or vice-versa, for each of the resulting M11, and at least one of said resulting M23 and M32 Mueller Matrix elements determined, and wherein each determined M13 and M31 is divided by M11, prior to using said resulting at least one of M13 and M31 values as data upon which to regress a model of said sample that includes free charge carrier longitudinal and transversal effective masses, concentration, mobility and type, thereby allowing their evaluation.

11. A method as in claim 10 in which the stage is present inside a chamber that comprises at least one selection from the group consisting of:
   at least an input port for use in controlling the atmospheric content and pressure inside said chamber; and
   a temperature controller inside said chamber;
and in which the method further comprises controlling at least one of:
   atmospheric content and/or pressure and/or temperature inside said chamber, while practicing step c).

12. A method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:
   a) providing an ellipsometer comprising:
      a source of a beam of electromagnetic radiation characterized by at least one wavelength in a selection from the group consisting of the: Vacuum Ultraviolet;
         Near-Ultraviolet;
         Mid-Ultraviolet;
         Visible;
         NIR;
         MIR;
         FIR; and
         THz ranges;
      a polarizer;
      a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s);
      an analyzer; and
      a detector of relevant electromagnetic radiation wavelengths; and
   further providing a source of a magnetic field;

b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;

c) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;

d) from data accumulated by said detector with the system adjusted as described in steps b) and c), evaluating anisotropic values for at least a partial Jones or Mueller Matrix; and e) from said anisotropic values for said at least a partial Jones or Mueller Matrix determining at least one of the free charge carrier longitudinal and/or transversal effective masses, and/or concentration, and/or mobility and/or type;

said method being characterized in that:

at least one of M32 and M23 is determined in addition to M11 by the procedure of data being determined by obtaining a first set of data with the sample back side in contact with said stage and then flipping said sample over so that it's surface is in contact with said stage and obtaining a second set of data; or by first placing the north pole of a permanent magnet near to the sample and obtaining a first set of data, and then placing the south pole of the same or another permanent magnet so that is near the sample and obtaining a second set of data, and then subtracting said second set of data from said first for each of the resulting M11, and at least one of said resulting M23 and M32 Mueller Matrix elements determined, prior to using said resulting at least one of the M23 and M32 and at least one of M23 and M32 values as data upon which to simultaneously regress a model of said sample that includes free charge carrier longitudinal and transversal effective masses, concentration, mobility and type, thereby allowing their evaluation.

13. A method as in claim 12 in which the stage is present inside a chamber that comprises at least one selection from the group consisting of:

at least an input port for use in controlling the atmospheric content and pressure inside said chamber; and a temperature controller inside said chamber;

and in which the method further comprises controlling at least one of:

atmospheric content and/or pressure and/or temperature inside said chamber, while practicing step c).

14. A method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:

a) providing an ellipsometer comprising:

a source of a beam of electromagnetic radiation characterized by at least one wavelength in a selection from the group consisting of the:

Vacuum Ultraviolet;
Near-Ultraviolet;
Mid-Ultraviolet;
Visible;
NIR;
MIR;
FIR; and
THz ranges;

a polarizer;

a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s);

an analyzer; and a detector of relevant electromagnetic radiation wavelengths; and further providing a source of a magnetic field;

b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;

c) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;

d) from data accumulated by said detector with the system adjusted as described in steps b) and c), evaluating anisotropic values for at least a partial Jones or Mueller Matrix; and e) from said anisotropic values for said at least a partial Jones or Mueller Matrix determining at least one of the free charge carrier longitudinal and/or transversal effective masses, and/or concentration, and/or mobility and/or type;

said method being characterized in that:

Mueller Matrix element M11, and at least one selection from the group of elements consisting of M12, M13, M23, or at least one selection from the group of elements consisting of M12, M13, M33 is evaluated by, for each selection, a selection from the group consisting of:

first placing said sample on said stage for supporting a sample with the back side thereof in contact with said stage and obtaining a first set of data, and second flipping said sample so that it's surface is in contact with said stage and obtaining a second set of data; and by first placing the north pole of a permanent magnet near to the sample and obtaining a first set of data, and second placing the south pole of the same or another magnet so that it is near the sample and obtaining a second set of data;

followed by subtracting the first from the second or the second from the first obtained set of data for each selection from the group of elements consisting of at least one selection from the group consisting of M12, M13, M23, or at least one selection from the group of elements consisting of M12, M13, M33;

followed by dividing said result(s) by M11, before, from said anisotropic value(s), determining at least one of the free charge carrier concentration and/or mobility.

15. A method as in claim 14 in which the stage is present inside a chamber that comprises at least one selection from the group consisting of:
   at least an input port for use in controlling the atmospheric content and pressure inside said chamber;
   a temperature controller inside said chamber;
and in which the method further comprises controlling at least one of:
   atmospheric content and/or pressure and/or temperature inside said chamber, while practicing step c).

16. An ellipsometer system comprising:
   a polarization state generator;
   a stage for supporting a sample having a substantially flat surface; and
   a polarization state detector;
such that in use said polarization state generator directs a polarized beam of electromagnetic radiation to interact with a sample on said stage for supporting a sample, which after said interaction presents as a beam of electromagnetic radiation that enters said polarization state detector, that in response produces sample characterizing data;
said ellipsometer system being distinguished in that said stage for supporting a sample is functionally a part of a resonate cavity that directs electromagnetic radiation that passes through a transparent or semi-transparent sample supported upon said stage having a substantially flat surface to be reflected back into said transparent or semi-transparent sample, such that when sample characterizing data is being accumulated by said polarization state detector, it is enhanced over what it would be otherwise as a result of coherent interaction in said transparent or semi-transparent sample between electromagnetic radiation incident thereupon provided by said polarization state generator, and electromagnetic radiation that reflects back into said transparent or semi-transparent sample as a result of said resonance effect, a resulting coherent combination of said two identified contributions of electromagnetic radiation in said sample then comprising said beam that enters said polarization state detector.

17. A system as in claim 16, which further comprises a magnet casing plate, such that in use a magnet can be secured thereto in a manner such that a magnetic field directed other than parallel thereto at the sample surface is presented to said sample, and which magnet casing plate and substantially flat surface associated with said magnet can be adjusted to be substantially parallel thereto at said substantially flat surface of said stage.

18. A system as in claim 17 in which said system further comprises a mechanism that enables aligning the substantially flat surface of said stage and the substantially flat surface associated with said magnet so that they are substantially parallel to one another by a tip/tilt procedure.

19. A system as in claim 17 in which it is said stage for supporting a sample that is caused to undergo said tip/tilt procedure to align the substantially flat surface associated with said magnet substantially parallel to the stage substantially flat surface.

20. A system as in claim 17 in which it is said substantially flat surface associated with said magnet that is caused to undergo said tip/tilt procedure to align the substantially flat surface associated with said magnet substantially parallel to the stage substantially flat surface.

21. A system as in claim 17 in which said substantially flat stage for supporting a sample is functionally a part of a resonate cavity surface associated with said magnet is caused be aligned substantially parallel to the stage substantially flat surface and then said resulting orientation is secured in place, followed by said tip/tilt procedure being practiced primarily to align said stage substantially flat surface so that desired angle-of-incidence and/or plane-of-incidence of said beam of electromagnetic radiation caused to be directed at said sample by said polarization state generator, is/are achieved.

22. A system as in claim 16 in which the resonance effect is enhanced by placing spacer material between the stage for supporting a sample and a sample supported thereby, or by application of a motor to adjust the distance between said stage and said sample.

23. A system as in claim 16, in which the resonance effect resulting from the relationship between the positioning of said stage for supporting a sample, and its location within said resonate cavity is adjustable, thereby allowing modulation of said positioning during application in date acquisition.

24. A method of evaluating at least one of free charge carrier longitudinal and/or transversal effective masses and/or concentration and/or mobility and/or free charge carrier type in a sample having a back side and a surface, said sample being transparent or semi-transparent or approaching substantially opaque beyond a distance from a surface thereinto at wavelength(s) utilized, said method comprising the steps of:
   a) providing an ellipsometer comprising:
      a source of a beam of electromagnetic radiation characterized by at least one wavelength in a selection from the group consisting of the:
      Vacuum Ultraviolet;
      Near-Ultraviolet;
      Mid-Ultraviolet;
      Visible;
      NIR;
      MIR;
      FIR; and
      THz ranges;
      a polarizer;
   a stage for supporting a sample, said stage comprising an adjustable surface that is capable of orienting a sample placed thereupon via adjustment of at least one selection from the group consisting of: stage tip, stage tilt and rotation thereof about an axis projecting substantially normal to said stage surface, to desired value(s);
      an analyzer; and
      a detector of relevant electromagnetic radiation wavelengths; and
      further providing a source of a magnetic field;
   b) placing a sample on said stage and adjusting said stage so that stage tip and/or stage tilt and/or rotation thereof about an axis projecting substantially normal to said stage surface are set to desired values, and so that the source of a magnetic field provides a magnetic field other than parallel thereto at said surface of said sample;
   c) while applying the source of a magnetic field to apply a selected magnitude magnetic field other than parallel thereto at the surface of said sample, causing said source of electromagnetic radiation to provide a beam of electromagnetic radiation of a desired wavelength which is caused to pass through said polarizer and assume a polarization state, interact with said sample, pass through said analyzer and enter said detector which detector produces sample characterizing data;

d) from data accumulated by said detector with the system adjusted as described in steps b) and c), evaluating anisotropic values for at least a partial Jones or Mueller Matrix; and e) from said anisotropic values for said at least a partial Jones or Mueller Matrix determining at least one of the free charge carrier longitudinal and/or transversal effective masses, and/or concentration, and/or mobility and/or type;

said method being characterized in that at least some Mueller Matrix elements are evaluated, said elements being M11, M12, M13, M14, M21, M22, M23, M23, M24, M31, M32 and M33, M34, M41, M42, M43 and M44, and wherein each Mueller Matrix element is divided by a normalizing factor prior to use in evaluating free charge carrier longitudinal and transversal effective masses, concentration, mobility and type.

25. A method as in claim 24, wherein the normalizing factor is matrix element M11.

26. A method as in claim 24, in which at least one off-diagonal Mueller matrix element selected from the group consisting of: M14, M24, M41 and M42, is evaluated.

* * * * *